(12) United States Patent
Gryska et al.

(10) Patent No.: US 8,835,180 B2
(45) Date of Patent: Sep. 16, 2014

(54) ORGANIC CHEMICAL SENSOR COMPRISING MICROPOROUS POLYMER, AND METHOD OF USE

(75) Inventors: Stefan H. Gryska, Woodbury, MN (US);
Nelson B. O'Bryan, Tamworth, NH (US); Neal A. Rakow, Woodbury, MN (US); Michael S. Wendland, North Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 351 days.

(21) Appl. No.: 12/681,741

(22) PCT Filed: Sep. 18, 2008

(86) PCT No.: PCT/US2008/076781
§ 371 (c)(1),
(2), (4) Date: Oct. 29, 2010

(87) PCT Pub. No.: WO2009/045733
PCT Pub. Date: Apr. 9, 2009

(65) Prior Publication Data
US 2011/0045601 A1    Feb. 24, 2011

Related U.S. Application Data

(60) Provisional application No. 60/977,707, filed on Oct. 5, 2007.

(51) Int. Cl.
*G01N 25/18* (2006.01)
*G01N 27/22* (2006.01)

(52) U.S. Cl.
CPC .................................. *G01N 27/221* (2013.01)
USPC ......................................... 436/149; 422/82.01

(58) Field of Classification Search
None
See application file for complete search history.

(56) References Cited

U.S. PATENT DOCUMENTS

| 5,482,678 | A | 1/1996 | Sittler |
| 5,512,882 | A | 4/1996 | Stetter et al. |
| 5,767,687 | A | 6/1998 | Geist |
| 5,857,250 | A | 1/1999 | Riley et al. |
| 5,965,451 | A | 10/1999 | Plog et al. |
| 6,864,692 | B1 | 3/2005 | Patel et al. |

(Continued)

FOREIGN PATENT DOCUMENTS

| JP | S6415646 | 1/1989 |
| JP | 06-281610 | 10/1994 |

(Continued)

OTHER PUBLICATIONS

Nagai, K., et al. Polyp[1-(trimethylsilyl)-1-propyne] and related polymers: synthesis, proprties and functions, 2001, Progress in Polymer Science, vol. 26, pp. 721-798.*

(Continued)

*Primary Examiner* — Robert Xu
(74) *Attorney, Agent, or Firm* — Kenneth B. Wood

(57) ABSTRACT

Applicant discloses a sensing element for sensing an organic chemical analyte, comprising a first electrode and a second electrode, and a microporous, hydrophobic, analyte-responsive dielectric material disposed at least in proximity to the first and second electrodes. The analyte-responsive dielectric material may be a polymer of intrinsic microporosity. An electrical property of the sensing element, such as capacitance, can be monitored in order to sense an organic chemical analyte.

18 Claims, 15 Drawing Sheets

(56) References Cited

U.S. PATENT DOCUMENTS

| | | |
|---|---|---|
| 2006/0237310 A1 | 10/2006 | Patel et al. |
| 2006/0246273 A1 | 11/2006 | McKeown et al. |
| 2006/0249402 A1 | 11/2006 | Snow et al. |
| 2008/0063575 A1 | 3/2008 | Rakow et al. |
| 2008/0070320 A1 | 3/2008 | Palazzotto et al. |

FOREIGN PATENT DOCUMENTS

| | | |
|---|---|---|
| JP | 2000-325955 | 11/2000 |
| WO | WO 2005/012397 A1 | 2/2005 |
| WO | WO 2005/113121 A1 | 12/2005 |

OTHER PUBLICATIONS

Gerwen, P. V., et al. Nanoscaled interdigitated electrode arrays for biochemical sensors, 1998, Sensors and Actuators B, vol. 49, pp. 73-80.*

Grate, J. W., Acoustic Wave Microsensor Arrays for Vapor Sensing; Chem. Rev. 2000 (100), 2627-2648 (2000).

Budd, P.M., et al., Free Volume and Intrinsic Microporosity in Polymers; J. Mater. Chem. 2005 (15), 1977-1986, (2005).

Budd et al., Polymers of Intrinsic Microporosity (PIMS): Robust, Solution-Processable, Organic Microporous Materials; Chem. Commun., 230-231 (2004).

McKeown et al., Polymers of Intrinsic Microporosity (PIMS); Chem. Eur. J., 11(9), 2610-2620, (2005).

* cited by examiner

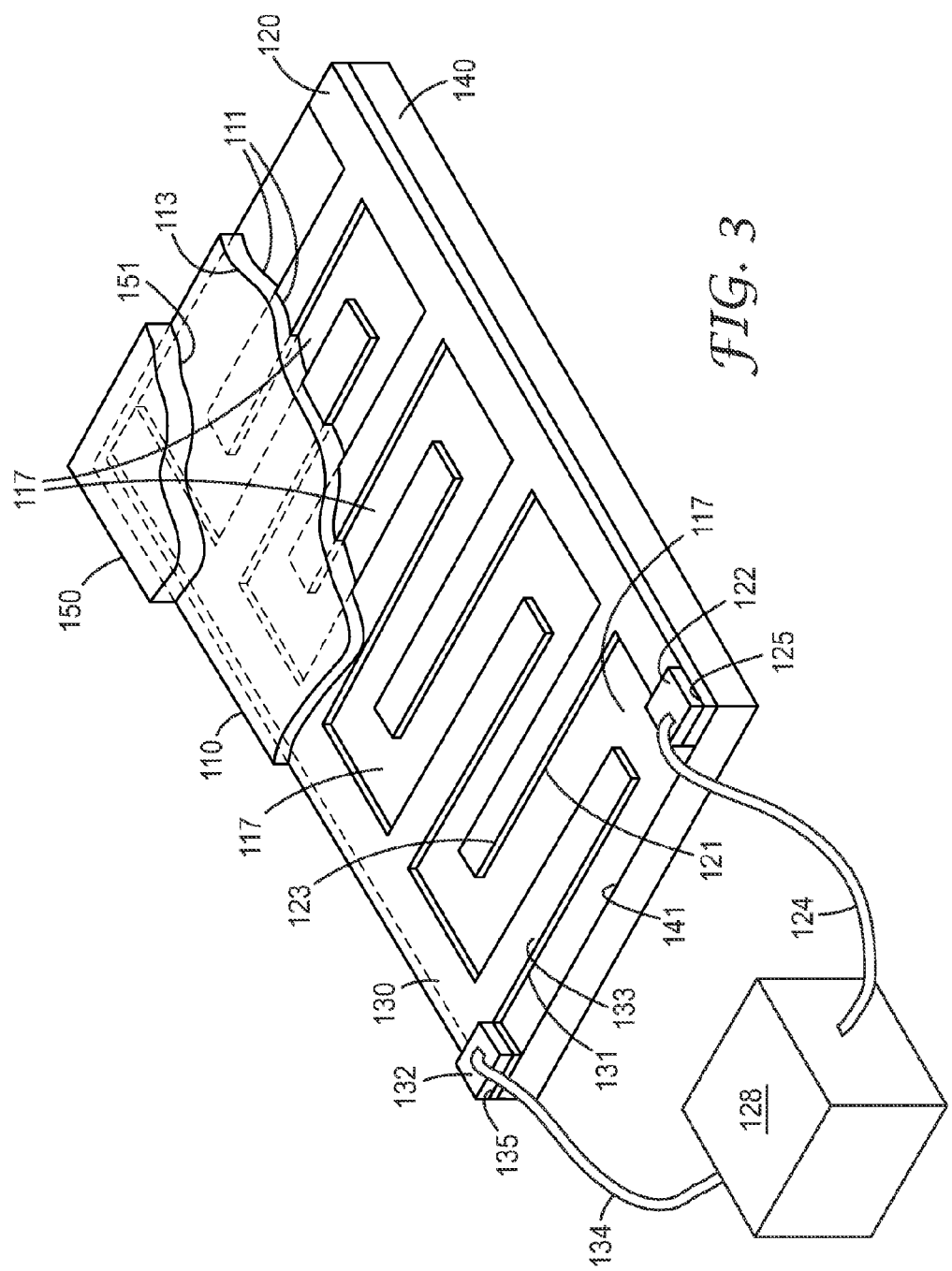

ORGANIC CHEMICAL SENSOR COMPRISING MICROPOROUS POLYMER, AND METHOD OF USE

CROSS REFERENCE TO RELATED APPLICATIONS

This application is a national stage filing under 35 U.S.C. 371 of PCT/US2008/076781, filed Sep. 18, 2008, which claims priority to U.S. Provisional Application No. 60/977,707, filed Oct. 5, 2007, the disclosures of which are incorporated by reference in their entirety herein.

BACKGROUND

The ability to detect chemical analytes, especially organic chemical analytes, is important in many applications, including environmental monitoring, and the like. Such detection and/or monitoring of organic molecules may find particular use in, for example, so called End of Service Life Indicators which are desired for personal protective equipment such as respirators.

Many methods for the detection of chemical analytes have been developed, for example optical, gravimetric, microelectromechanical, and so on. In particular, sensors that monitor electrical properties such as capacitance, impedance, resistance, etc., have been developed. Often, such sensors rely on the change that occurs in the electrical properties of a material upon adsorption of an analyte onto, or absorption of an analyte into, the material.

For example, U.S. Patent Application Publication 2006/0249402 to Snow et al. discloses a sensing device having a bottom electrode, a dielectric on the bottom electrode, a grid of nanoelectrodes on the dielectric, and a top electrode in electrical contact with the grid. The nanoelectrodes may be a network of carbon nanotubes. Such an arrangement is described by Snow et al. as being capable of exhibiting a capacitance change in the presence of a chemical analyte.

U.S. Patent Application Publication 2006/0237310 to Patel et al. discloses a device that is described as being able to detect various target analytes by adsorption or absorption of the analyte in a chemical sensing material such that an electrical property (e.g. capacitance, resistance, etc.) is altered in a manner detectable by circuitry associated with the sensing electrode pair coated with the chemical sensing materials.

U.S. Pat. No. 5,512,882 to Stetter and Maclay discloses a sensor whose impedance changes upon exposure to a vapor of a selected chemical substance. The sensor comprises a polymer whose physical structure is altered by the vapor (e.g., through expansion or disintegration). The sensor further comprises electrically conductive elements that are interspersed with the polymer. Changes can be measured by an impedance-measuring circuit.

U.S. Pat. No. 5,482,678 to Sittler discloses a sensor comprising a material which expands in the presence of an organic liquid, gas or vapor. The material is applied to a support surface such that upon expansion, the support deflects and changes the distance between two capacitor plates, thereby changing an electrical capacity between the plates.

U.S. Pat. No. 5,965,451 to Plog and Maunz discloses a gas sensor for selective detection of hydrocarbons, having a capacitive element and a gas-permeable sensitive layer as a dielectric. The sensitive layer is precious-metal-doped zeolite which has a regular crystalline structure made of primary pores whose diameter is on the order of the gas-kinetic diameter of the gas molecules to be detected.

SUMMARY

Applicant discloses a sensing element which is suitable for detecting or monitoring organic chemical analytes in an environment, for example in ambient atmosphere. Such a sensing element comprises an analyte-responsive dielectric material which is in proximity to first and second electrodes. In this context, an analyte-responsive dielectric material means a material that is capable of absorbing an organic chemical analyte, and that can exhibit a measurable change in an electrical property upon absorbing the organic analyte into the material. In one embodiment, the analyte-responsive dielectric material exhibits a change in dielectric constant upon absorption of the analyte, such that a change in capacitance of the sensing element can be observed.

In one embodiment, the analyte-responsive dielectric material is a polymer of intrinsic microporosity. Such a material may provide advantages in terms of high sensitivity to low levels of organic analytes, rapid response to organic analytes, and low sensitivity to water. Without being limited by theory or mechanism, applicant postulates that the performance that applicant has found in use of polymers of intrinsic microporosity as analyte-responsive dielectric materials, may be due to any or all of several properties: hydrophobicity, an optimum amount of porosity, a microporous pore volume that encompasses an optimum pore size range, and the ability of the polymers of intrinsic microporosity to be cast from solution so as to form an analyte-responsive dielectric layer.

In various embodiments, polymers of intrinsic microporosity can be formulated via the use of any combination of monomers that leads to a very rigid polymer and gives a polymer within which there are sufficient structural features to induce a contorted structure. In various embodiments, such materials can comprise organic macromolecules comprised of first generally planar species connected by rigid linkers, said rigid linkers having a point of contortion such that two adjacent first planar species connected by the linker are held in non-coplanar orientation. In various embodiments, such materials can comprise organic macromolecules comprised of first generally planar species connected by rigid linkers predominantly to a maximum of two other said first species, said rigid linkers having a point of contortion such that two adjacent first planar species connected by the linker are held in non-coplanar orientation. In various embodiments, such a point of contortion may comprise a spiro group, a bridged ring moiety or a sterically congested single covalent bond around which there is restricted rotation.

In one aspect, herein is disclosed a sensing element for sensing an organic chemical analyte, comprising: a first electrode and a second electrode; and, a microporous, hydrophobic, analyte-responsive dielectric material disposed at least in proximity to the first and second electrodes, wherein the microporous, hydrophobic analyte-responsive dielectric material is a polymer of intrinsic microporosity. In one embodiment, at least one of the electrodes is permeable to an organic chemical analyte. In a further embodiment, the permeable electrode is discontinuous. In an additional embodiment, the permeable electrode is patterned. In various embodiments, the sensing element can comprise a backing layer and/or a cover layer in proximity to at least one of the electrodes. In various embodiments, the sensing element can comprise a parallel plate capacitor configuration, or an interdigitated capacitor configuration.

In another aspect, herein is disclosed a sensor for sensing an organic chemical analyte, comprising: a sensing element that comprises a first electrode and a second electrode and a microporous, hydrophobic, analyte-responsive dielectric material disposed at least in proximity to the first and second electrodes, wherein the microporous, hydrophobic analyte-responsive dielectric material is a polymer of intrinsic microporosity; and, an operating circuit in electrical communication with the first and second electrodes, wherein the operating circuit is capable of applying a voltage to the first and second electrodes and is capable of detecting a change in an electrical property of the sensing element.

In yet another aspect, herein is disclosed a method of sensing organic chemical analytes, comprising: providing a sensor that comprises; a sensing element that comprises a first electrode and a second electrode and a microporous, hydrophobic, analyte-responsive dielectric material disposed at least in proximity to the first and second electrodes, wherein the microporous, hydrophobic, analyte-responsive dielectric material is a polymer of intrinsic microporosity; and, an operating circuit in electrical communication with the first and second electrodes, wherein the operating circuit is capable of applying a voltage to the first and second electrodes and is capable of detecting a change in an electrical property of the sensing element; exposing the sensing element to an environment potentially containing one or more organic chemical analytes; applying a voltage to the first and second electrodes; and, monitoring an electrical property of the sensing element.

These and other aspects of the invention will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

FIG. 3 is a perspective view of an exemplary sensing element in an interdigitated configuration.

Like reference symbols in the various figures indicate like elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings.

DETAILED DESCRIPTION

Although terms such as "top", bottom", "upper", lower", "front" and "back", and "first" and "second" may be used in this disclosure, it should be understood that those terms are used in their relative sense only.

Sensing Element

Figure 1:
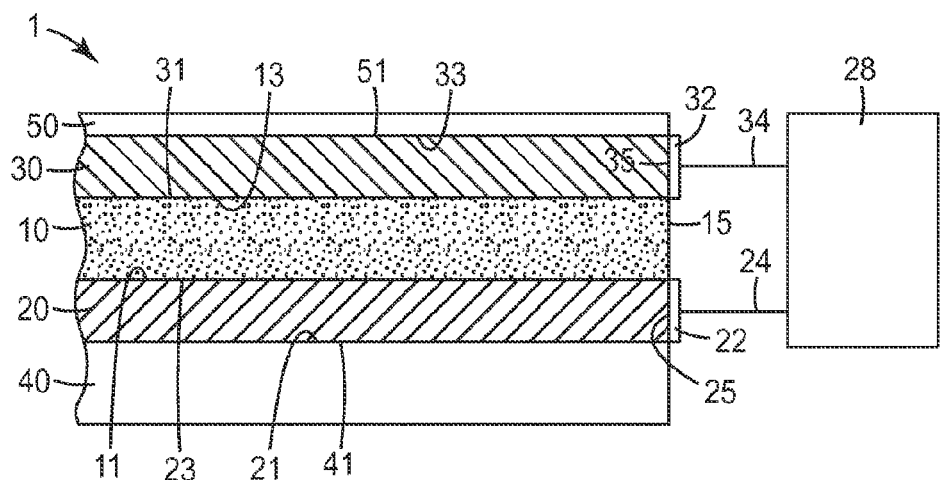
FIG. 1 is a side view of an exemplary sensing element in a parallel-plate configuration.
Figure 2:
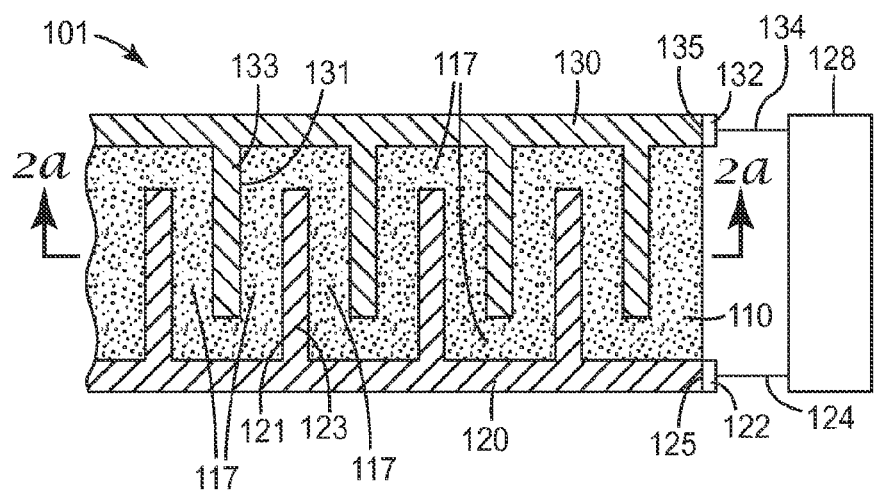
FIG. 2 is a top view of an exemplary sensing element in an interdigitated configuration.

With reference to FIGS. 1 and 2, herein is disclosed a sensing element 1/101 that comprises at least an analyte-responsive dielectric layer 10/110 in proximity to a first electrode 20/120 and a second electrode 30/130. These components, and features and properties thereof, as well as other optional components and the features and properties thereof, will be discussed in turn. These discussions will refer to both FIG. 1, which depicts an exemplary sensing element based on the general configuration of a parallel plate capacitor, and FIGS. 2, 2a, and 3, which depict exemplary sensing elements based on the general configuration of an interdigitated capacitor. For clarity, the various components have been given different reference numbers (generally, incremented by 100) in the Figs. depicting the different general configurations. However, it should be understood that the structure, composition and properties of the various components, may be applicable to sensing elements of any capacitive design, unless otherwise stated.

The sensing element 1/101 is configured such that the analyte-responsive dielectric layer 10/110 is in sufficiently close proximity to the first electrode 20/120 and the second electrode 30/130 that the analyte-responsive dielectric material contained in the layer will be capable of interacting with an electric field that is established by the electrodes. In operation of sensing element 1/101, analyte-responsive dielectric layer 10/110 exhibits a change in an electrical property upon absorption of one or more analytes. In one embodiment, the electrical property is capacitance or a capacitance-related property as described below. Such a change in a capacitance-related property can be measured by imparting a charge differential between the first electrode 20/120 and the second electrode 30/130 (e.g., by imparting a voltage differential to the electrodes) and monitoring the property of the sensing element in response to the presence of the analyte. Such monitoring can be done by the use of an operating circuit 28/128, as described later herein.

The terms "capacitance" and "capacitance-related property" encompass any electrical property and the measurement thereof that is in general associated with the imparting of an electrical charge (whether static or time variant) and the monitoring of an electrical property during and/or after the imparting of the charge. Such properties include not only capacitance, but also impedance, admittance, resistance, conductance, etc., and may be measured according to various methods known in the art.

Analyte-Responsive Dielectric Layer

The analyte-responsive dielectric layer 10/110 (the term "layer" being used generically and encompassing any physical configuration) comprises at least in part an analyte-responsive dielectric material. In this context, the term "analyte-responsive dielectric material" means a material that is capable of absorbing an organic chemical analyte, and that can exhibit a measurable change in some electrical property of the material upon absorbing the organic analyte into the material.

Polymers of Intrinsic Microporosity

In one embodiment, the analyte-responsive dielectric material is chosen from the family of materials comprising so-called "polymers of intrinsic microporosity" (hereafter called PIMs). Such polymers include, but are not limited to, those disclosed in "Polymers of Intrinsic Microporosity (PIMs): Robust, Solution-Processable, Organic Microporous Materials," Budd et al., *Chem. Commun.*, 2004, pp. 230-231; in "Polymers of Intrinsic Microporosity (PIMs)," McKeown et al., *Chem. Eur. J.*, 2005, 11, No. 9, 2610-2620; in US Patent Application Publication 2006/0246273 to McKeown et al.; and in Published PCT application No. WO 2005/012397A2 to McKeown et al.

PIMs can be formulated via the use of any combination of monomers that lead to a very rigid polymer within which there are sufficient structural features to induce a contorted structure. In various embodiments, PIMs can comprise organic macromolecules comprised of generally planar species connected by rigid linkers, said rigid linkers having a point of contortion such that two adjacent planar species connected by the linker are held in non-coplanar orientation. In further embodiments, such materials can comprise organic macromolecules comprised of first generally planar species connected by rigid linkers predominantly to a maximum of two other said first species, said rigid linkers having a point of contortion such that two adjacent first planar species connected by the linker are held in non-coplanar orientation. In various embodiments, such a point of contortion may comprise a spiro group, a bridged ring moiety or a sterically congested single covalent bond around which there is restricted rotation.

In a polymer with such a rigid and contorted structure, the polymer chains are unable to pack together efficiently, thus the polymer possesses intrinsic microporosity. Thus, PIMs have the advantage of possessing microporosity that is not significantly dependent on the thermal history of the material. PIMs thus may offer advantages in terms of being reproducibly manufacturable in large quantities, and in terms of not exhibiting properties that change upon aging, shelf life, etc.

In this context, the terms "microporous" and "microporosity" mean that the material has a significant amount of internal, interconnected pore volume, with the mean pore size (as characterized, for example, by sorption isotherm procedures) being less than about 100 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed. Without being limited by theory or mechanism, applicant considers that the disclosed sensing element 1/101, relying on a microporous dielectric material, may have advantageous properties with regard to the sensing of an organic analyte, in that a measurable change in an electrical property of the dielectric material may be caused by the presence of the analyte molecules in the pores. Thus, it may be possible to detect the analyte without the analyte molecules being required to be solubilized in the polymeric material itself to a sufficient extent to cause a change in a property of the polymeric material such as swelling and/or expansion (although such a phenomenon may also occur and may also contribute to a measurable electrical response). Such a microporous nature of the analyte-responsive dielectric material may contribute to increased sensitivity of the dielectric material to small amounts of organic analyte.

In various embodiments, the PIM comprises a porosity of at least about 10%, at least about 20%, or at least about 30% (as characterized, for example, by sorption isotherm techniques, such as those using instruments available under the trade mark Autosorb from Quantachrome Instruments of Boynton Beach, Fla.). Such porosity can provide good response to low levels of organic chemical analytes. However, the material should not have such a high pore volume that it is difficult to avoid electrical shorting or arcing between the first electrode 20/120 and the second electrode 30/130. Thus, in various embodiments, the material comprises a porosity of at most about 90%, at most about 60% or at most about 40%.

Again without being limited by theory or mechanism, the size and distribution of the internal pores may be such that at least some of the organic analyte molecules in at least some of the pores may form a more highly condensed state (e.g. a quasi-liquid state) than they would otherwise be in (e.g., than they would be in the environment in which the analyte is monitored). This may result in analyte molecules collecting in the internal pores in larger numbers and/or at a higher concentration than they are present in the environment being monitored; in addition, or instead, the analyte molecules in this state may exhibit a higher dielectric constant (relative permittivity) than in an uncondensed vaporous or gaseous state. Thus, a sensing element based on a microporous analyte-responsive dielectric material with appropriately chosen size and distribution of pores may exhibit superior sensitivity to small quantities of organic analyte. In various embodiments, the PIM comprises an average pore size of less about 50 nm, less than about 20 nm, or less than about 10 nm. In various embodiments, the PIM comprises an average pore size of greater than about 0.3 nm, greater than about 0.5 nm, or greater than about 1.0 nm.

In one embodiment, the PIM is a hydrophobic material (e.g. a hydrophobic organic polymeric material), that will not absorb liquid water to an extent that the material swells significantly or otherwise exhibits a significant change in a physical property. Such hydrophobic properties are useful in providing an organic analyte sensing element that is relatively insensitive to the presence of water. The material may however comprise relatively polar moieties for specific purposes.

In one embodiment, the PIM comprises a continuous matrix. Such a matrix is defined as an assembly (e.g. a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g. zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g. a latex), or by coating and drying of a sol-gel mixture, may not comprise a continuous network as defined by applicant. However, if such a latex, sol-gel, etc., layer can be consolidated such that individual particles are no longer discernible, nor is it possible to discern areas of the assembly that were obtained from different particles, such a layer may then meet applicant's definition of a continuous matrix.

In certain embodiments, PIMs are soluble in common organic solvents and thus are amenable to conventional deposition processes such as coating.

In certain embodiments, after a PIM material is deposited (e.g., coated) or otherwise formed so as to comprise an analyte-responsive dielectric layer, the material may be crosslinked using a suitable crosslinking agent, for example bis(benzonitrile)palladium(II) dichloride. This process may render the analyte-responsive dielectric layer insoluble in organic solvents, and/or may enhance certain physical properties such as durability, abrasion resistance, etc., which may be desirable in certain applications.

In certain embodiments, the PIMs may be blended with other materials. For example, the PIM may be blended with a material that itself is not an analyte-responsive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form a analyte-responsive dielectric blend layer comprising both the PIM and the other polymer(s). PIMs may also be blended with a material that is an analyte-responsive dielectric material (for example, zeolites, activated carbon, silica gel, hypercrosslinked polymer networks and the like). Such materials may comprise insoluble materials that are suspended in a solution comprising of a PIMs material. Coating and drying of such a solution/suspension may provide a composite analyte-responsive dielectric layer comprising both the PIM material and the additional analyte-responsive dielectric material.

In various embodiments, an additional layer or layers of material that is not an analyte-responsive dielectric material may be provided in proximity to the analyte-responsive dielectric layer. Such a layer or layers may be provided for any of a variety of reasons, e.g. as a protective layer, as a tie layer to improve adhesive, and so on.

In various embodiments, multiple individual layers of analyte-responsive dielectric material can be used. For example, multiple layers of PIM materials can be used. Alternatively, one or more layers of some other analyte-responsive dielectric material can be used in addition to a layer of PIM material. The various layers of analyte-responsive dielectric material can be in direct contact with each other; or, they can be separated by a layer or layers present for some other purpose (e.g., passivation layers, tie layers, as described herein).

Electrodes

With reference to FIGS. 1 and 2, the first electrode 20/120 and second electrode 30/130 can comprise any suitable conductive material. Combinations of different materials (conductive and/or nonconductive) can be used, as different layers or as a mixture, as long as sufficient overall conductivity is provided (e.g., the electrode material comprises a constant resistivity of less than about $10^{-2}$ ohms-meter). Examples of materials that can be used to make the first electrode and/or second electrode include, but are not limited to, organic materials, inorganic materials, metals, alloys, and various mixtures and composites comprising any or all of these materials. In certain embodiments, coated (for example, vapor coated, sputter coated, etc.) metals or metal oxides, or combinations thereof, may be used. Suitable conductive materials include for example aluminum, tin, indium-tin oxide, gold, silver, platinum, palladium, copper, and the like. In one embodiment, both electrodes comprise the same material; in an alternative embodiment, the first and second electrodes comprise different materials, In various embodiments either or both of the electrodes can be permeable to an organic analyte. Such electrode permeability may be particularly useful in the case of a sensing element which is configured in the general manner of a parallel-plate capacitor as shown in FIG. 1. In such a case, if second electrode 30 is permeable, an organic analyte can enter analyte-responsive dielectric layer 10 through major surface 13, rather than having to enter the analyte-responsive dielectric layer 10 by way of edge 15, which might be a slower process. Likewise, if first electrode 20 is permeable, an organic analyte may be able to enter analyte-responsive dielectric layer 10 through major surface 11 (however, if backing 40 is not permeable to the analyte, it may not be useful to provide first electrode 20 in a permeable configuration).

In various embodiments, an electrode can be analyte-permeable by virtue of being discontinuous. In this context, the term discontinuous does not imply that the electrode comprises units (spots, islands, etc.) that are not in electrical contact with each other. Rather, discontinuous means that within the overall boundaries of the electrode, some areas do not contain conductive material. Such a discontinuous electrode may be microscopically discontinuous. For example, an electrode can be formed by the deposition (e.g., by coating, ink jet printing, etc.) of a sol comprising particles (e.g. nanoparticles) of a conductive material. In such a case, the electrode comprises conductive particles that are in sufficient contact to ensure that the electrode is conductive, but with sufficient spaces in between the particles to render the electrode permeable to an organic analyte. In other embodiments, an electrode can comprise a microscopically discontinuous structure. For example, if a conductive material comprises vapor coated metal (which is typically impermeable), the conductive metal can be deposited in a pattern (for example, in a grid pattern, or in a "comb" pattern as disclosed in Example 1) rather than as a continuous layer.

With reference to FIGS. 1 and 2, an electrically accessible area 25/125 of first electrode 20/120, and an electrically accessible area 35/135 of second electrode 30/130, are provided such that it is possible to connect an operating circuit 28/128 to the sensing element via these areas. Such electrically accessible areas can be provided in any convenient location. For example, such electrically accessible areas are shown on an edge of the electrodes in the exemplary illustrations of FIGS. 1 and 2, and are shown on a major surface (123 and 133) of the electrodes in the exemplary illustration of FIG. 3. In one embodiment, a connecting device (e.g. a contact pad or tab) 22/122 is positioned in contact with (e.g. attached to) the accessible area of the first electrode 20, such that electrical connection can be made (for example via attachment of wires 24/124) between sensing element 1/101 and an operating circuit 28/128. A similar connecting device 32/132 can be likewise positioned in contact with the accessible area of the second electrode 30.

Exemplary Sensing Elements and Methods of Making Parallel-Plate Configuration

In one embodiment, a sensing element 1 can be produced which is configured in the general manner of a parallel-plate capacitor as shown in an exemplary manner in the cross sectional view of FIG. 1. In such a configuration, the sensing element comprises two generally planar, parallel, opposing electrodes, with the analyte-responsive dielectric layer being present in between the electrodes and preventing direct electrical contact between the two electrodes.

In an exemplary process for making such a sensing element, a backing 40 is provided (which may be a continuous slab, layer or film of material) that is in proximity to at least one of the electrodes and that may serve to provide physical strength and integrity to the finished sensing element. Any suitable material may be used, including glass, ceramic, plastic, etc. In large scale production, a polymeric film (such as polyester) may be used. In some embodiments, the backing is an analyte-permeable material (for example, silicone rubber, a microporous membrane, etc.).

In one embodiment, a conductive layer that serves as first electrode 20 is provided on backing 40. The conductive layer may comprise any of the materials mentioned above, including blends or mixtures of conductive and nonconductive materials, and may be deposited by any suitable method, including but not limited to spin coating, dip coating, screen printing, transfer coating, sputter-coating, physical vapor deposition, chemical vapor deposition, or a combination of two or more of such methods. In an alternate embodiment, the conductive layer may be provided by placing a premade film (e.g. a metal foil, conductive tape, etc.) atop backing 40. This first electrode 20 may be provided as a continuous layer or as a discontinuous layer, as previously described.

In one embodiment, the conductive layer is provided such that a first surface 21 of electrode 20 is in proximity to, and/or in contact with, at least a portion of the first surface 41 of backing 40. In an alternative embodiment, an optional layer is present between at least a part of first surface 21 of electrode 20, and first surface 41 of backing 40. Such an optional layer may be used for any purpose (such as improving the bond between first electrode 20 and backing 40), as long as the layer does not interfere with the functioning of the sensing element 1.

In producing sensing element 1, an analyte-responsive dielectric layer 10 is also provided. In one embodiment, the analyte-responsive dielectric layer 10 is provided such that first major surface 11 of layer 10 is in direct contact with at least a portion of the second surface 23 of first electrode 20 (leaving at least a portion of first electrode 20 accessible for connection to an operating circuit).

In one embodiment, the analyte-responsive dielectric material is placed in proximity to the first electrode by a coating process, for example, including but not limited to solvent coating, spin coating, dip coating, transfer coating, screen printing, and the like. In certain embodiments, the dielectric material is deposited in such a manner as to minimize the presence of defects, pinholes, etc., that might serve to compromise the performance of the sensing element. In a particular embodiment, the analyte-responsive dielectric layer comprises a polymer of intrinsic microporosity that is deposited by coating a solution of PIM material upon a suitable substrate and allowing the solution to dry so as to form a solid layer comprising the PIM material.

An analyte-responsive dielectric layer 10 can also be provided by other methods. For example, a preformed film of analyte-responsive dielectric material can be placed upon the second surface of the first electrode. In an alternative embodiment, the analyte-responsive dielectric material can be provided in particulate form (e.g. as a powder, as a suspension, or as a sol) and deposited in such a form onto a first electrode so as to form a particulate coating. If desired, such a material can be consolidated so as to form a continuous matrix of analyte-responsive dielectric material.

In various embodiments, a second electrode 30 can be formed by placing a second conductive layer in proximity to the analyte-responsive dielectric layer 10. The second electrode 30 may comprise conductive materials as described above, and may be deposited according to methods described above. In certain embodiments (particularly in the case in which backing 40 is impermeable to an analyte), the second electrode may comprise a discontinuous structure (again as previously described) so as to be permeable to an organic analyte.

With reference to FIG. 1, an optional protective cover or barrier layer 50 can be provided in proximity to at least one of the electrodes. In one embodiment, cover layer 50 can be placed atop second electrode 30 (leaving an area of second electrode 30 accessible for electrical contact). Any such cover layer 50 should not significantly interfere with the functioning of sensing element 1. For example, if the sensing element is configured such that an analyte of interest must pass through cover layer 50 in order to reach the analyte-responsive dielectric layer 10, the cover layer should be sufficiently permeable to the analyte.

Cover layer 50 may be deposited by any method known in the art, including coating (e.g. spin coating, dip coating, solvent coating, vapor coating, transfer coating, screen printing, flexographic printing, and the like). In an alternate embodiment, cover layer 50 can comprise a premade layer (e.g. a film or tape) that is placed upon second electrode 30. In one embodiment, cover layer 50 is provided such that first surface 51 of cover layer 50 is in direct contact with at least a portion of second surface 33 of second electrode 30. The second surface of the cover layer may be the outermost surface of the sensing element, or may itself receive additional coatings or layers if desired.

In one embodiment, the second surface 23 of first electrode 20 and first major surface 11 of the analyte-responsive dielectric layer 10 are in direct contact, with no interposing layer(s) therebetween. Likewise in one embodiment, the first surface 31 of second electrode 30 and second major surface 13 of the analyte-responsive dielectric layer 10 are in direct contact, with no interposing layer(s) therebetween. Such embodiments are pictured in FIG. 1. However, it is also contemplated that other, optional layers may be present between the first electrode 20 and the analyte-responsive dielectric layer 10, and/or between the second electrode 30 and the analyte-responsive dielectric layer 10. In such a case, either or both of the electrodes may not be in direct contact with some or all of a surface of the analyte-responsive dielectric material. For example, a tie layer or layers may be used to improve the bonding between an electrode and the analyte-responsive dielectric layer. Or, a passivation layer or layers (for example, a layer of silicon dioxide) may be placed in between a surface of the analyte-responsive dielectric layer and an electrode surface, in order to minimize the possibility of arcing between the electrodes. In some embodiments, multiple such optional layers may be used; alternatively a single layer may serve multiple functions. Any such optional layer or layers such as the aforementioned tie layers, passivation layers, protective layers, cover layers, etc., may be used, for whatever purpose, as long as they do not significantly interfere with the desired functioning of the sensing element. For example, an optional layer should be sufficiently permeable to an analyte of interest if the sensing element is configured such that the analyte must pass through the optional layer in order to reach the analyte-responsive dielectric layer 10.

In general, the edges of the various layers can be aligned flush with each other (as depicted in the exemplary embodiment of FIG. 1). Alternatively, various layers may overlap other layers, and/or the edges of certain layers may be recessed relative to other layers.

In the deposition of the analyte-responsive dielectric material atop first electrode 20, an electrically accessible area 25 should be provided on first electrode 20, to enable electrical contact between the electrode and an operating circuit. Similarly, if a cover layer is placed atop second electrode 30, an electrically accessible area 35 should be similarly provided. Such electrically accessible areas can be provided in any convenient location. In one embodiment, a connecting device (e.g. a contact pad, tab, or the like) 22 may be placed in electrical contact with accessible area 25 of first electrode 20. Similarly, a connecting device 32 may be placed likewise in contact with accessible area 35 of second electrode 30.

Interdigitated Configuration

Figure 2A:
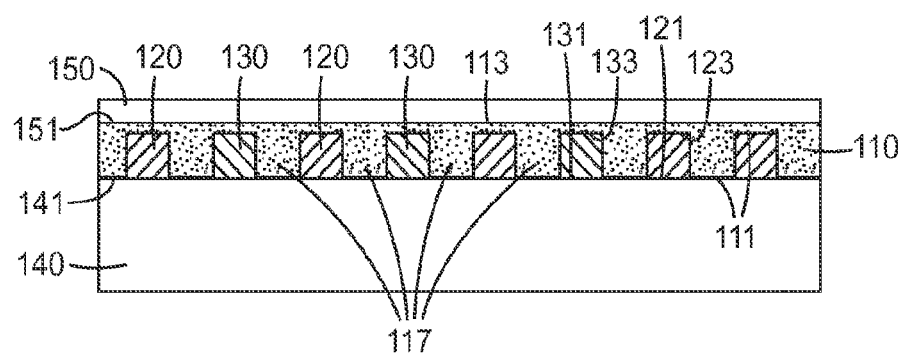
FIG. 2a is a cross sectional view of the exemplary sensing element of FIG. 2, taken along the line marked "2a" in FIG. 2.

In another embodiment, a sensing element can be produced that is configured in the general manner of an interdigitated capacitor. Exemplary embodiments of interdigitated sensing elements are shown in the top view of FIG. 2, in the cross-sectional view of FIG. 2a (taken along the line marked "2a" in FIG. 2), and in the perspective view of FIG. 3. In this context, the term interdigitated encompasses any arrangement comprising at least two electrodes present in an interdigitated configuration. Such configurations include interdigitated comb patterns (such as depicted in FIGS. 2, 2a and 3), as well as interdigitated spiral or serpentine patterns as are well known in the art. All of these designs have the common characteristic that (at least) two electrodes are present in a largely coplanar interdigitated arrangement with an analyte-responsive dielectric layer present in proximity to the electrodes such that when an electric field is established between the electrodes, an analyte-responsive dielectric material contained in the layer is capable of interacting with the electric field. The analyte-responsive dielectric layer/material may be provided between the electrodes (i.e. in the plane of the two electrodes and interposed in the closest linear path between any two points of approach of the first and second electrodes). Alternatively, the analyte-responsive dielectric layer/material may be provided such that, while not coplanar with the electrodes, the analyte-responsive dielectric material is exposed at least to the fringing electric field that is established between adjacent sections of the two electrodes. In still another alternate embodiment, the analyte-responsive dielectric layer may be provided in both locations.

Interdigitated electrodes can be provided by the deposition of conductive material in two interdigitated patterns by any of the methods (e.g. masked vapor deposition, screen-printing, ink-jet printing) that are well known for patterned deposition of materials. The particular geometric/dimensional properties of the electrode patterns (spacing, height, length etc.) may be designed as desired.

In one embodiment, interdigitated electrodes are provided on a backing 140 which may be comprised of materials described above. First electrode 120 and second electrode 130 are typically provided on the same backing 140. In one embodiment (shown in FIGS. 2, 2a and 3), first surface 121 of first electrode 120, and first surface 131 of second electrode 130, are both in direct contact with at least some portion of the first surface 141 of backing 140. In an alternative embodiment (not pictured), an optional layer or layers can be present between the electrode 120 and/or 130 and the backing 140, similar to the optional layers described above, and subject to the same issues and constraints.

As illustrated in the exemplary embodiments of FIGS. 2, 2a, and 3, the patterned deposition of first electrode 120 and second electrode 130 may leave an area of surface 141 of backing 140, (or, of the surface of any optional layer thereupon) exposed. An analyte-responsive dielectric layer can then be deposited onto backing 140, via similar methods to those described above with reference to sensing elements of a parallel-plate type. The deposited analyte-responsive dielectric material will thus fill the spaces between the two electrodes (e.g. spaces 117 depicted in FIGS. 2, 2a, and 3). Thus, in this embodiment a first surface 111 of the analyte-responsive dielectric layer 110 will be in direct contact with at least a portion of surface 141 of backing 140. The deposition process may also cause the analyte-responsive dielectric layer 110 to cover, and be in contact with, second surface 123 of the first electrode, and second surface 133 of the second electrode, as depicted in FIGS. 2a and 3 (unless the deposition is performed selectively, e.g. with one or both of the electrodes masked). Thus, in various embodiments, the first surface 111 of analyte-responsive dielectric layer 110 is in direct contact with second surface 123 of first electrode 120, and/or with second surface 133 of second electrode 130.

In alternative embodiments, an optional layer (not shown in FIG. 2, 2a, or 3) may be provided atop the second surface 123 of first electrode 120, and/or atop the second surface 133 of first electrode 130. (In this embodiment, direct contact between first surface 111 of analyte-responsive dielectric layer 110 and second surface 123 of first electrode 120, and/or second surface 133 of second electrode 130, may not occur). Such an optional layer may serve similar purposes (protective, etc.) to those described earlier. However, in an interdigitated type sensing element, an optional layer atop one or both electrodes may not necessarily need to be permeable to the analyte since the analyte may not need to penetrate through the an optional layer to reach areas 117 of the analyte-responsive dielectric layer 110.

In one embodiment, an optional cover layer 150 (which may serve as a protective layer, insulating layer, decorative layer, etc.) may be deposited atop the second surface 113 of the analyte-responsive dielectric layer 110. Any such cover layer should not significantly interfere with the functioning of the sensing element (e.g., it should be sufficiently permeable to an analyte of interest). This cover layer may comprise a coating deposited by any known coating process (e.g. spin coating, dip coating, solvent coating, vapor coating, transfer coating, screen printing, flexographic printing, and the like). In an alternate embodiment, cover layer 150 can comprise a premade layer (e.g. a film or tape) that is placed atop second surface 113 of layer 110.

In the deposition of the analyte-responsive dielectric material (and of any optional cover layer), an electrically accessible area 125 should be provided on first electrode 120, and an accessible area 135 on second electrode 130, to allow electrical contact between each electrode and an operating circuit. Such electrically accessible areas can be provided in any convenient location. For example, such electrically accessible areas 125 and 135 are shown on an edge of an electrode in the exemplary illustration of FIG. 2, and are shown on surfaces 123 and 133 of an electrode in the exemplary illustration of FIG. 3.

In one embodiment, a connecting device (e.g. a contact pad, tab, or the like) 122 may be placed in electrical contact with accessible area 125 of first electrode 120. Similarly, a connecting device 132 may be placed likewise in contact with accessible area 135 of second electrode 130.

Operating Circuit

Upon absorption of sufficient analyte by the analyte-responsive dielectric layer, a detectable change in an electrical property associated with the sensing element (including but not limited to, capacitance, impedance, admittance, current, or resistance) may occur. Such a detectable change may be detected by an operating circuit 28/128 that is in electrical communication with the first and second electrodes. In this context, "operating circuit" refers generally to an electrical apparatus that can be used to apply a voltage to the first electrode and the second electrode (thus imparting a charge differential to the electrodes), and/or to monitor an electrical property of the sensing element, wherein the electrical property may change in response to the presence of an organic analyte. In various embodiments, the operating circuit may monitor any or a combination of inductance, capacitance, voltage, resistance, conductance, current, impedance, phase angle, loss factor, or dissipation.

Such an operating circuit may comprise a single apparatus which both applies voltage to the electrodes, and monitors an electrical property. In an alternative embodiment, such an operating circuit may comprise two separate apparatuses, one to provide voltage, and one to monitor the signal. An operating circuit may be connected to first electrode 20/120 and to second electrode 30/130 by wires 24/124 and 34/134. In an alternative embodiment, an operating circuit may be provided in direct contact with the first and/or the second electrode, either via connecting devices 22/122 and 32/132, or by contacting some portion of the operating circuit directly to an electrically accessible area of each electrode. For example, an operating circuit can be provided that resides on a circuit board or a flexible circuit (either of which can also serve as backing 40/140). A first electrode can then be deposited directly onto circuit board/backing 40 such that it is in direct contact with a portion of the operating circuit.

An operating circuit 28/128 may include, for example, a power supply (which may comprise a battery or a hardwired power source; alternatively, power may be provided indirectly via, for example, charging of an RFID circuit that is built into the operating circuit). An operating circuit 28/128 may also include one or more microprocessors configured to control the charging of the electrodes and/or to monitor changes in one or more electrical properties of a charged sensing electrode pair. Also present may be analog-to-digital converters, memory devices for storing data derived from the sensing element, software for operating the sensing element, components that provide data logging and/or one- or two-way telemetry capability, and so on.

Analytes

A sensing element such as herein disclosed can be used to detect and/or monitor (whether qualitatively or quantitatively) the presence of an organic analyte or analytes. Such analytes can include, but are not limited to, hydrocarbons, fluorocarbons, alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile and the like. Analytes can be relatively nonpolar organic molecules or relatively polar organic molecules. Analytes can be so-called vapors; i.e. molecules that are capable of forming a solid or liquid under the ambient conditions of temperature and pressure that the analyte is experiencing (e.g. toluene, acetone, heptane, etc.). Analytes can be so-called gases; i.e. molecules that are not normally capable of forming a liquid or solid under ambient conditions (although such molecules may still comprise a more highly condensed state in the internal pores of the analyte-responsive dielectric material, as discussed above). Such gases may include methane, ethane, and the like. Mixtures of organic analyte molecules may in some circumstances be detected.

The invention is further illustrated by means of the following examples. All numerical values in the following examples should be regarded as being modified by the term "approximately".

EXAMPLES

Gel Permeation Chromatography (GPC)

Molecular weight of various materials was measured using Gel Permeation Chromatography (GPC). Each sample was prepared by the addition of 10 mL of THF to approximately 25 mg of material. The solution was filtered using a 0.25 micrometer Teflon syringe filter. 100 microliters of solution was injected into a six column set (Jordi Associates mixed bed and 500A 25 cm long columns, Jordi Associates Inc., Bellingham, Mass.) in combination with a Waters 2695™ Separation Module (Waters Corp., Milford, Mass.). The Waters 2695™ operated at 35° C., using THF as the eluent, flowing at a rate of 1.0 mL/min. Changes in concentration were detected with a Shimadzu Scientific RID-10A refractive index detector (Shimadzu Scientific Inc., Columbia, Md.) in combination with a Wyatt DAWN EOS multi-angle laser light scattering detector (Wyatt Technology, Co., Santa Barbara, Calif.). The molecular weight calculations were completed with Wyatt's ASTRA software, first by calculating the dn/dc's of each sample, and then using this value to calculate the molecular weight. The results are expressed as $M_w$ (weight average molecular weight) and $M_n$ (number average molecular weight).

Preparation of PIM 1

PIM material was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials*, 2004, Vol. 16, No. 5, pp. 456-459. 19.31 grams of 5,5',6,6'-tetrahydroxy-3,3,3',3'-tetramethyl-1,1'-spirobisindane were combined with 11.34 g of tetrafluoroterephthalonitrile, 47.02 g potassium carbonate, and 500 milliliters of N,N-dimethylformamide, and the mixture was reacted at 65° C. for 48 hours. The resulting polymer was dissolved in tetrahydrofuran, precipitated three times from methanol, and then dried under vacuum at room temperature. A yellow solid product was obtained having a weight-average molecular weight of approximately 95,000 and a number-average molecular weight of approximately 64,300, as determined by gel permeation chromatography analysis using light scattering detection.

Preparation of PIM 2

PIM material was prepared following the same general procedure described for PIM 1. 19.31 grams of 5,5',6,6'-tetrahydroxy-3,3,3',3'-tetramethyl-1,1'-spirobisindane were combined with 11.34 g of tetrafluoroterephthalonitrile, 47.02 g potassium carbonate, and 500 milliliters of N,N-dimethylformamide, and the mixture was reacted at 65° C. for 48 hours. The resulting polymer was dissolved in tetrahydrofuran, precipitated three times from methanol, and then dried under vacuum at room temperature. A yellow solid product was obtained having a weight-average molecular weight of approximately 109,000 and a number-average molecular weight of approximately 73,600, as determined by gel permeation chromatography analysis using light scattering detection.

Preparation of PIM 3

PIM material was prepared following the same general procedure described for PIM 1. 5.62 grams of 5,5',6,6'-tetrahydroxy-3,3,3',3'-tetramethyl-1,1'-spirobisindane were combined with 3.30 g of tetrafluoroterephthalonitrile, 13.68 g potassium carbonate, and 150 milliliters of N,N-dimethylformamide, and the mixture was reacted at 65° C. for 62 hours. The resulting polymer was dissolved in tetrahydrofuran, precipitated two times from methanol, and then dried under vacuum at room temperature. A yellow solid product was obtained having a weight-average molecular weight of approximately 65,300 and a number-average molecular weight of approximately 35,600, as determined by gel permeation chromatography analysis using light scattering detection.

Preparation of PIM 4

PIM material was prepared following the same general procedure described for PIM 1 except using recrystallized 5,5',6,6'-tetrahydroxy-3,3,3',3'-tetramethyl-1,1'-spirobisindane. 5,5',6,6'-tetrahydroxy-3,3,3',3'-tetramethyl-1,1'-spirobisindane purchased from Aldrich was recrystallized from THF/heptane (1.2:1) prior to use in polymerization. 33.44 grams of recrystallized 5,5',6,6'-tetrahydroxy-3,3,3',3'-tetramethyl-1,1'-spirobisindane and 19.80 g of tetrafluoroterephthalonitrile were dissolved in 900 mL of anhydrous N,N-dimethylformamide. Nitrogen was bubbled through this stirred solution for 1 hour. 81.45 grams of potassium carbonate was added to the monomer solution. The resulting mixture was vigorously stirred at 67° C. for 67.5 hours. The resulting polymer was dissolved in tetrahydrofuran, precipitated two times from methanol, and then dried under vacuum at 65° C. A yellow solid product was obtained having a weight-average molecular weight of approximately 58,900 and a number-average molecular weight of approximately 35,800, as determined by gel permeation chromatography analysis using light scattering detection.

Preparation of Sample 1

A cleaned piece of glass (2.5 cm by 2.5 cm) was coated with a continuous (unpatterned) coating of aluminum using a CHA Industries Mark-50 evaporator operated at a base pressure of $1 \times 10^{-5}$ torr and No. A-2049 aluminum pellets (99.995% purity, 6×6 mm, from Cerac Inc.). The aluminum coating was deposited at a rate of 15 angstroms/second. The final thickness was 100 nm. A diamond-tipped pen was used to score the aluminized glass approximately 5 mm from one edge. The scored piece of aluminized glass was taped down to a 5 cm by 5 cm piece of glass such that there was a margin of masked aluminum surface all around the edge of the sample. Care was taken so that the masked area was still approximately 2 mm from the score line. A 4 weight % solution of PIM 1 in chlorobenzene was prepared and spin coated onto the masked sample at 1200 rpm for 2 minutes using a WS-400B-8NPP-Lite Single Wafer spin processor manufactured by Laurell Technologies, Corp. North Wales, Pa. A second electrode was made using a silver nanoparticle suspension (30 nm mean particle diameter, suspended in methanol) available under the designation Silverjet DGP-40LT-25C from Advanced Nano Products Co., Ltd. (South Korea). A 0.5 g quantity of this as-received suspension was mixed with 1 milliliter of methanol. The diluted silver nanoparticle suspension was spin coated onto the PIM film at 1000 rpm for 2 minutes. The tape was removed from the masked sample, and the sample was heated in a conventional drying oven for 3 hours at 150° C. By attaching a premade mask to the sample, a series of 1 mm wide by 4 mm long aluminum tabs were made on the sample on the side nearest the score line such that the aluminum tabs connected the second electrode to the bottom aluminum electrode. Aluminum evaporation was carried out in a Kurt Lesker vacuum system at a base pressure of $1 \times 10^{-6}$ torr. Aluminum, with a purity of 99.999%, purchased from Alfa Aesar, was thermally evaporated from a tungsten boat at a rate of 5 Å/sec. The final thickness was 100 nm. This procedure thus provided a glass (backing) layer with a first electrode comprising continuous aluminum, to which an operating circuit could be contacted. Atop the aluminum electrode was an analyte-responsive dielectric layer comprising a PIM material (approximately 600 nm thick). Atop the PIM material was a second electrode comprising a microscopically-discontinuous (thus analyte-permeable) silver layer (approximately 300 nm thick). This second electrode was in contact with the smaller aluminum-coated area via aluminum tabs, such that the second electrode could be connected with the operating circuit by attaching the circuit to the smaller aluminum-coated area.

Preparation of Sample 2

A cleaned piece of glass was coated with aluminum, scored, masked and coated with PIM 1 as described for Sample 1. The tape was removed from the masked sample, and the sample was heated in a conventional drying oven for 1 hour at 150° C. A patterned second electrode was inkjet printed on top of the PIM material to complete the construction of this sample. In order to inkjet print the second electrode, a bitmap image (702 dots per inch) was created in Adobe Photoshop and then downloaded to an XY deposition system. The printhead used for depositing the silver was a Dimatix SX3-128 printhead with a 10 pL drop volume and 128 jets/orifices, the printhead assembly being approximately 6.5 cm long with 508 micron jet to jet spacing. The silver nanoparticle sol used to construct this electrode was obtained from Cabot under the designation AG-IJ-G-100-S1. This silver nanoparticle sol was approximately 15-40 wt % ethanol, 15-40 wt % ethylene glycol, and 20 wt % silver. The sample was held securely during the inkjet printing process by use of a porous aluminum vacuum platen. Upon completion of printing, the sample was removed from the porous aluminum vacuum platen and placed on a Thermolyne hot plate for 15 minutes at 125° C.

The inkjet printed silver electrode comprised a comb pattern that consisted of a solid rectangle with lines extending from one edge. The rectangular portion of the printed electrode was positioned such that a portion of the rectangle was atop a portion of the smaller aluminum-coated area (such that electrical contact with the top electrode could be achieved by attaching a wire to the smaller aluminum-coated area), with the remainder of the second printed electrode being atop the PIM material. The lines on the electrode were designed to be approximately 8.3 mm long and approximately 102 microns wide. The gap between the lines was designed to be approximately 152 microns. (It should be noted that all of these dimensions were the nominal dimensions of the bitmap image and not the actual 'printed' dimensions).

This procedure provided a glass backing layer with a first electrode comprising continuous aluminum. Atop the aluminum electrode was an analyte-responsive dielectric layer comprising a PIM material, with a second electrode comprising a silver layer in a comb pattern residing atop the PIM layer. An operating circuit could be attached to the electrodes in similar manner to that described with reference to Sample 1.

Preparation of Sample 3

An interdigitated electrode transducer was fabricated by vapor depositing copper (at a thickness of approximately 43 microns) onto a polyimide backing layer (of thickness approximately 52 microns). The electrodes comprised interdigitated comb patterns of 0.5 cm by 0.5 cm in dimension connected to conductive leads. The electrode lines had a width of approximately 20 microns and a pitch of approximately 40 microns. The interdigitated transducer was taped down to a 5 cm by 5 cm piece of glass such that two ends of the transducer were covered with tape with one of the pieces of tape completely covering the conductive leads. A 4 weight % solution of PIM 1 (prepared as described above) in chlorobenzene was spin coated onto the masked sample at 2500 rpm for 2 minutes. The tape was removed from the masked sample. This procedure thus provided a polyimide backing layer bearing first and second interdigitated copper electrodes. Atop the interdigitated electrodes was an analyte-responsive dielectric layer comprising a PIM material of approximately 400 nm thickness.

Preparation of Sample 4

An interdigitated electrode transducer was fabricated by vapor depositing gold onto a polymeric backing layer. The gold was then photolithographically defined to comprise interdigitated comb patterns of 1.2 cm by 1.0 cm in dimension connected to conductive leads. The electrode lines had a pitch of approximately 320 microns. The interdigitated transducer was taped down to a 5 cm by 5 cm piece of glass such that two ends of the transducer were covered with tape with one of the pieces of tape completely covering the conductive leads. A 4 weight % solution of PIM 2 (prepared as described above) in chlorobenzene was spin coated onto the masked sample at 1200 rpm for 2 minutes. The tape was removed from the masked sample, and the sample was heated in a conventional drying oven for 1 hour at 100° C. This procedure thus provided a polymeric backing layer bearing first and second interdigitated gold electrodes. Atop the interdigitated electrodes was an analyte-responsive dielectric layer comprising a PIM material of approximately 400 nm thickness.

Preparation of Sample 5

An interdigitated electrode transducer was fabricated by vapor depositing gold onto a polymeric backing layer. The gold was then photolithographically defined to comprise interdigitated comb patterns of 1.2 cm by 1.0 cm in dimension connected to conductive leads. The electrode lines had a pitch of approximately 120 microns. The interdigitated transducer was taped down to a 5 cm by 5 cm piece of glass such that two ends of the transducer were covered with tape with one of the pieces of tape completely covering the conductive leads. A 4 weight % solution of PIM 2 (prepared as described above) in chlorobenzene was spin coated onto the masked sample at 1200 rpm for 2 minutes. The tape was removed from the masked sample, and the sample was heated in a conventional drying oven for 1 hour at 100° C. This procedure thus provided a polymeric backing layer bearing first and second interdigitated gold electrodes. Atop the interdigitated electrodes was an analyte-responsive dielectric layer comprising a PIM material of approximately 400 nm thickness.

Preparation of Sample 6

An interdigitated electrode transducer was fabricated by vapor depositing gold onto a polymeric backing layer. The gold was then photolithographically defined to comprise interdigitated comb patterns of 1.2 cm by 1.0 cm in dimension connected to conductive leads. The electrode lines had a pitch of approximately 80 microns. The interdigitated transducer was taped down to a 5 cm by 5 cm piece of glass such that two ends of the transducer were covered with tape with one of the pieces of tape completely covering the conductive leads. A 4 weight % solution of PIM 2 (prepared as described above) in chlorobenzene was spin coated onto the masked sample at 1200 rpm for 2 minutes. The tape was removed from the masked sample, and the sample was heated in a conventional drying oven for 1 hour at 100° C. This procedure thus provided a polymeric backing layer bearing first and second interdigitated gold electrodes. Atop the interdigitated electrodes was an analyte-responsive dielectric layer comprising a PIM material of approximately 400 nm thickness.

Preparation of Sample 7

An interdigitated electrode transducer was fabricated by vapor depositing gold onto a polymeric backing layer. The gold was then photolithographically defined to comprise interdigitated comb patterns of 1.2 cm by 1.0 cm in dimension connected to conductive leads. The electrode lines had a pitch of approximately 40 microns. The interdigitated transducer was taped down to a 5 cm by 5 cm piece of glass such that two ends of the transducer were covered with tape with one of the pieces of tape completely covering the conductive leads. A 4 weight % solution of PIM 2 (prepared as described above) in chlorobenzene was spin coated onto the masked sample at 1200 rpm for 2 minutes. The tape was removed from the masked sample, and the sample was heated in a conventional drying oven for 1 hour at 100° C. This procedure thus provided a polymeric backing layer bearing first and second interdigitated gold electrodes. Atop the interdigitated electrodes was an analyte-responsive dielectric layer comprising a PIM material of approximately 400 nm thickness.

Preparation of Sample 8

A gold-coated poly(ethylene terephthalate) (PET) (ST504, E. I. DuPont de Nemours and Company, Wilmington, Del.) substrate was prepared by thermal evaporation (DV-502A, Denton Vacuum, Moorestown, N.J.) of 20 angstroms of chromium followed by 100 nm of gold.

The master tool used for molding an elastomeric stamp was generated by preparing patterns of photoresist (Shipley1818, Rohm and Haas Company, Philadelphia, Pa.) on a 10 cm diameter silicon wafer using photolithography. The elastomeric stamp was molded against the master tool by pouring uncured poly(dimethylsiloxane) (PDMS, Sylgard™184, Dow Corning, Midland, Mich.) over the tool to a thickness of approximately 3.0 mm. The uncured silicone in contact with the master was degassed by exposing to a vacuum and then cured for 2 hours at 70° C. After peeling from the master tool, a PDMS stamp was provided with a relief pattern comprising raised features approximately 1.8 microns in height. With this stamp, interdigitated electrode transducers having electrode lines with a width of approximately 3 microns and a pitch of approximately 10 microns were produced.

To make the interdigitated electrode transducer, the structured stamp was inked by contacting its back side (flat surface without relief pattern) with a solution of 10 mM octadecylthiol ("ODT" O0005, TCI AMERICA, Wellesley Hills, Mass.) in ethanol for 20 hours. The gold coated PET film was contacted to the stamp relief patterned surface, which was face up, by first contacting an edge of the film sample to the stamp surface and then rolling the film into contact across the stamp using a roller with a diameter of approximately 3.0 cm. The gold coated PET film was then left in contact with the stamp for 20 seconds thereby placing a patterned self-assembled monolayer (SAM) of thiols on the gold surface. The gold coated PET film was then peeled from the stamp. The gold coated PET film with printed pattern was then immersed into an etchant solution for 50 seconds for selective etching and metal patterning. The etchant comprised 1.0 grams of thiourea (T8656, Sigma-Aldrich, St. Louis, Mo.), 0.54 milliliters of concentrated hydrochloric acid (HX0603-75, EMD Chemicals, Gibbstown, N.J.), 0.5 milliliters of hydrogen peroxide (30%, 5240-05, Mallinckrodt Baker, Phillipsburg, N.J.), and 21 grams of deionized water. After patterned etching of the gold, residual chromium was etched using a solution of 2.5 grams of potassium permanganate (PX1551-1, EMD Chemicals, Gibbstown, N.J.), 4 grams of potassium hydroxide (484016, Sigma-Aldrich, St. Louis, Mo.), and 100 milliliters of deionized water. The interdigitated transducer was taped down to a 5 cm by 5 cm piece of glass such that two ends of the transducer were covered with tape with one of the pieces of tape completely covering the conductive leads. A 4 weight % solution of PIM 2 (prepared as described above) in chlorobenzene was spin coated onto the masked sample at 1200 rpm for 2 minutes. The tape was removed from the masked sample, and the sample was heated in a conventional drying oven for 1 hour at 100° C. This procedure thus provided a polymeric backing layer bearing first and second interdigitated gold electrodes. Atop the interdigitated electrodes was an analyte-responsive dielectric layer comprising a PIM material of approximately 400 nm thickness.

Preparation of Sample 9

Using a mask, a 1.2 cm by 2.0 cm corner of a cleaned piece of glass (2.5 cm by 2.5 cm) was evaporatively coated with a continuous (unpatterned) coating of first 10 nm of titanium followed by 100 nm of aluminum using the equipment described above in the Preparation of Sample 1. A chlorobenzene solution of PIM 3 was used to spin coat a 750 nm thick layer on top of the entire glass piece. A swab with a small amount of acetone was used to remove the PIM layer to expose a small corner of the bottom aluminum electrode for connection to an operating circuit. Using the inkjet printing method described above for the Preparation of Sample 2, a 0.9 cm by 1.5 cm rectangle of a silver nanoparticle sol (Cabot AG-IJ-G-100-S1) was printed on top of the PIM layer positioned such that only a 0.9 cm by 1.0 cm portion of the rectangle was directly over the bottom aluminum electrode. Upon completion of printing, the sample was placed on a Thermolyne hot plate for 15 minutes at 125° C. To improve the ability to connect to the top electrode, the top inkjet printed electrode was thickened (only in the area that was not directly over the bottom aluminum electrode) using the Advanced Nano Products Co., Ltd. silver nanoparticle suspension (Silverjet DGP-40LT-25C from Advanced Nano Products Co., Ltd.). This thickening step was accomplished by simply using a paint brush to brush the nanoparticle suspension on top of the desired area. After the thickening step, the sample was dried in a conventional drying oven for 1 hour at 150° C. This procedure provided a glass backing layer with a first electrode comprising continuous aluminum. Atop the aluminum electrode was an analyte-responsive dielectric layer comprising a PIM material, with a second electrode comprising a microscopically-discontinuous (thus analyte-permeable) silver layer residing atop the PIM layer. An operating circuit could be attached to the electrodes in similar manner to that described with reference to Sample 1.

Preparation of Sample 10

Using a mask, a 1.2 cm by 2.0 cm corner of a cleaned piece of glass (2.5 cm by 2.5 cm) was evaporatively coated with a continuous (unpatterned) coating of first 10 nm of titanium followed by 100 nm of aluminum using the equipment described above in the Preparation of Sample 1. A chlorobenzene solution of PIM 4 was used to spin coat a 400 nm thick layer on top of the entire glass piece. A swab with a small amount of acetone was used to remove the PIM layer to expose a small corner of the bottom aluminum electrode for connection to an operating circuit. Using the inkjet printing method described above for the Preparation of Sample 2, a 0.9 cm by 1.5 cm rectangle of a silver nanoparticle sol (Cabot AG-IJ-G-100-S1) was printed on top of the PIM layer positioned such that only a 0.9 cm by 1.0 cm portion of the rectangle was directly over the bottom aluminum electrode. Upon completion of printing, the sample was placed on a Thermolyne hot plate for 15 minutes at 125° C. To improve the ability to connect to the top electrode, the top inkjet printed electrode was thickened (only in the area that was not directly over the bottom aluminum electrode) using the Advanced Nano Products Co., Ltd. silver nanoparticle suspension (Silverjet DGP-40LT-25C from Advanced Nano Products Co., Ltd.). This thickening step was accomplished by simply using a paint brush to brush the nanoparticle suspension on top of the desired area. After the thickening step, the sample was dried in a conventional drying oven for 1 hour at 150° C. This procedure provided a glass backing layer with a first electrode comprising continuous aluminum. Atop the aluminum electrode was an analyte-responsive dielectric layer comprising a PIM material, with a second electrode comprising a microscopically-discontinuous (thus analyte-permeable) silver layer residing atop the PIM layer. An operating circuit could be attached to the electrodes in similar manner to that described with reference to Sample 1.

Testing of Sample 1

A simple flow-through custom built delivery system was used to deliver known concentrations of acetone to the sample for measurement. Teflon tubing was used throughout the delivery system. Nitrogen was sparged through a container that contained acetone in liquid form and held at a constant temperature as to provide a nitrogen stream that was saturated with acetone. The liquid acetone was kept at a constant temperature using a chiller from Fisher Scientific, and the temperature at which to keep the chiller in order to create a saturated gaseous stream of acetone was calculated using the Handbook of Vapor Pressure (Yaws, C. I. Gulf Publishing: Houston, 1994). The saturated gaseous acetone stream was diluted with additional nitrogen by use of a series of mass flow controllers. The concentration of acetone in the gaseous stream was calibrated by use of an infrared spectrometer (available under the designation Miran Sapphire from ThermoElectron of Waltham, Mass.). The gaseous acetone stream was introduced into a sample chamber (held at controlled temperature) containing Sample 1. The first and second electrodes of the sample were connected to an operating circuit that comprised an LCR meter (available under the designation Instek Model 821 LCR meter from Instek America, Corp.

Figure 4:
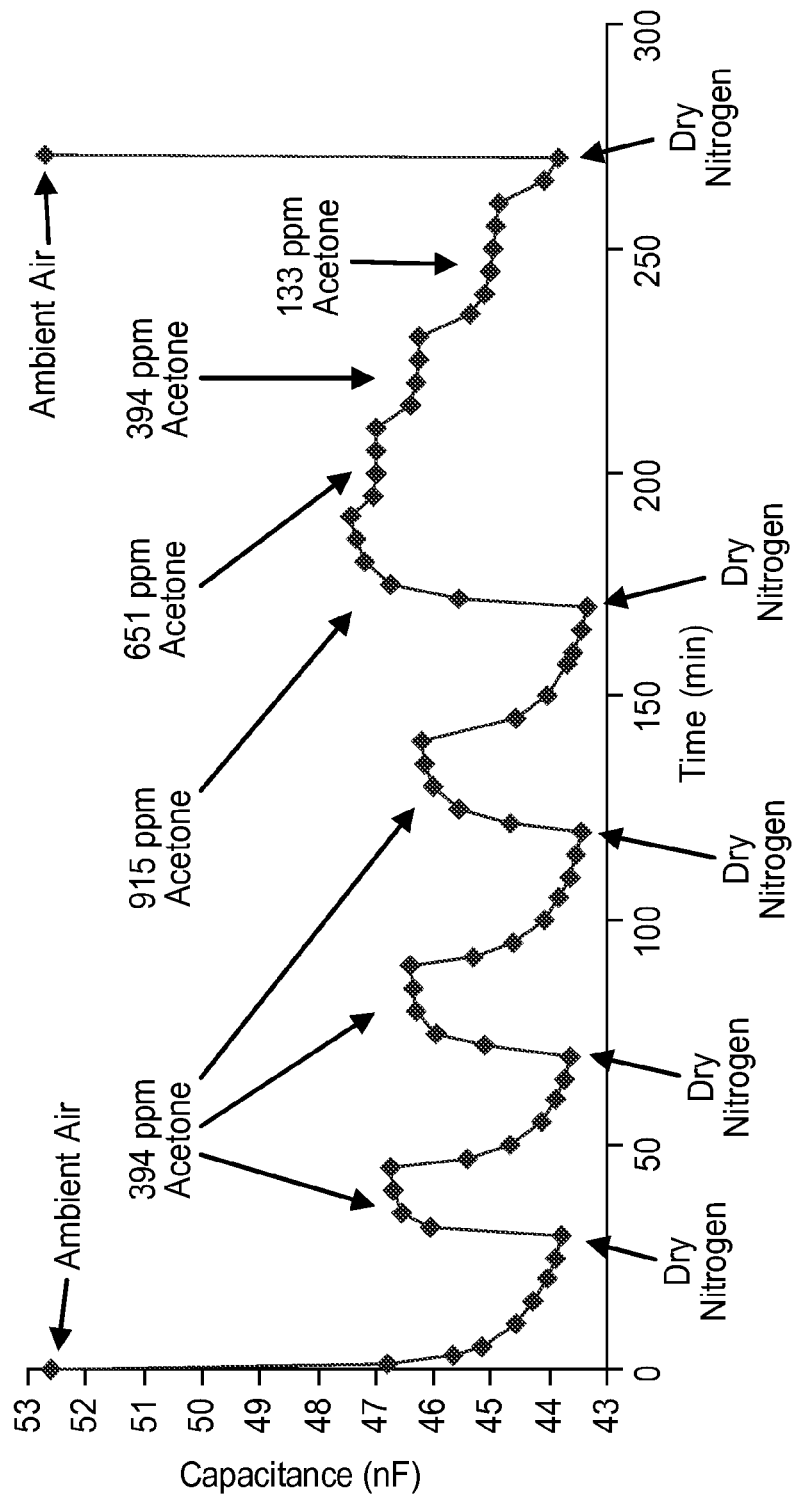
FIG. 4 is a plot of the measured capacitance of an exemplary sensing element of a parallel-plate configuration, as a function of time of exposure to various levels of an organic analyte.

Chino, Calif.) using alligator clips. The changes in capacitance (in nanoFarads) of the sample were monitored at a frequency of 10 kilohertz at specific time intervals during the entire course of the vapor test (as shown in FIG. 4).

The sample was first placed in the unsealed test chamber in order to measure the initial capacitance of the sample at ambient conditions (room air, approximately 58% relative humidity). The sample was then exposed to dry nitrogen (approximately 8% relative humidity and 20° C.) starting at time=0. The test chamber was then sealed and a gaseous nitrogen stream containing 394 ppm of acetone was introduced into the test chamber for a first period of time. Then, the test chamber was returned to a dry nitrogen environment. The exposure to 394 ppm of acetone was repeated two more times with the sample being exposed to an acetone-free dry nitrogen stream after each acetone exposure. After the last dry nitrogen exposure, the sample was exposed to a dry nitrogen stream with 915 ppm of acetone. After a period of time, the acetone concentration was reduced step-wise to 651 ppm, then to 394 ppm, then to 133 ppm. Thereafter, the sample was exposed to dry nitrogen. The test chamber was then opened, and the sample was exposed to ambient conditions (air, 51% relative humidity).

Testing of Sample 2

Figure 5:
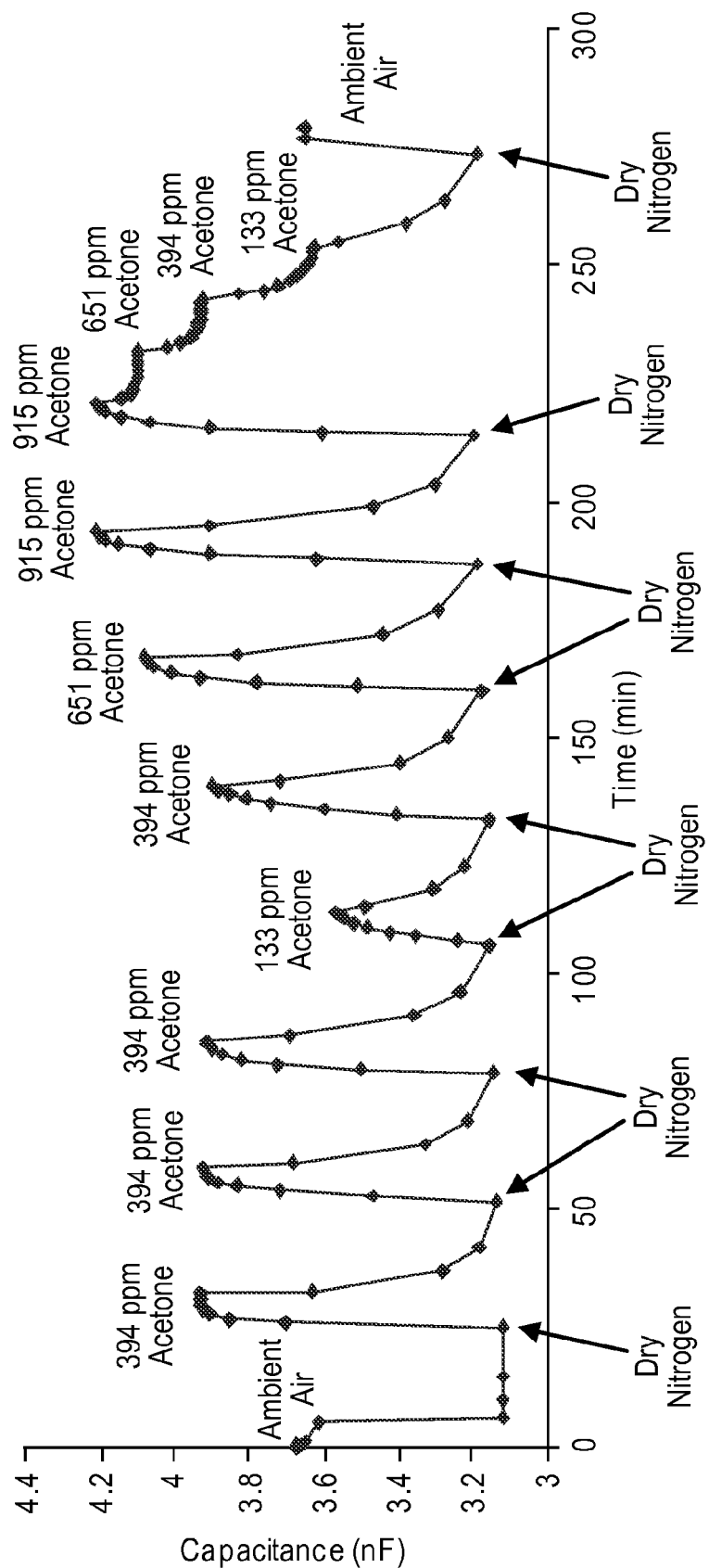
FIG. 5 is a plot of the measured capacitance of an exemplary sensing element of a parallel-plate configuration, as a function of time of exposure to various levels of an organic analyte.

Sample 2 (prepared as described above) was tested using the same set-up described with reference to Sample 1. The changes in capacitance (in nanoFarads) of the sample were monitored at a frequency of 10 kilohertz at specific time intervals during the entire course of the vapor test (as shown in FIG. 5). At the beginning of the test the sample was placed in the unsealed test chamber in order to measure the initial capacitance of the sample at ambient room conditions (air, approximately 64% relative humidity). The sample was then exposed to dry nitrogen (approximately 8% relative humidity, 20° C.). The test chamber was sealed and a dry nitrogen stream containing 394 ppm of acetone was introduced into the test chamber. Then, the test chamber was returned to a dry nitrogen environment. The exposure to 394 ppm of acetone was repeated two more times, each time followed by exposure to dry nitrogen. Thereafter, the sample was exposed to successive nitrogen streams containing 133, 394, 651 and 915 ppm, with the sample being returned to an acetone-free dry nitrogen environment in between each exposure. After the last dry nitrogen exposure, the sample was exposed to a dry nitrogen stream with 915 ppm of acetone. After a period of time, the acetone concentration was reduced step-wise to 651 ppm, then to 394 ppm, then to 133 ppm. Thereafter, the sample was exposed to dry nitrogen. The test chamber was then opened, and the sample was exposed to ambient conditions (air, 64% relative humidity).

Testing of Sample 3

Figure 6:
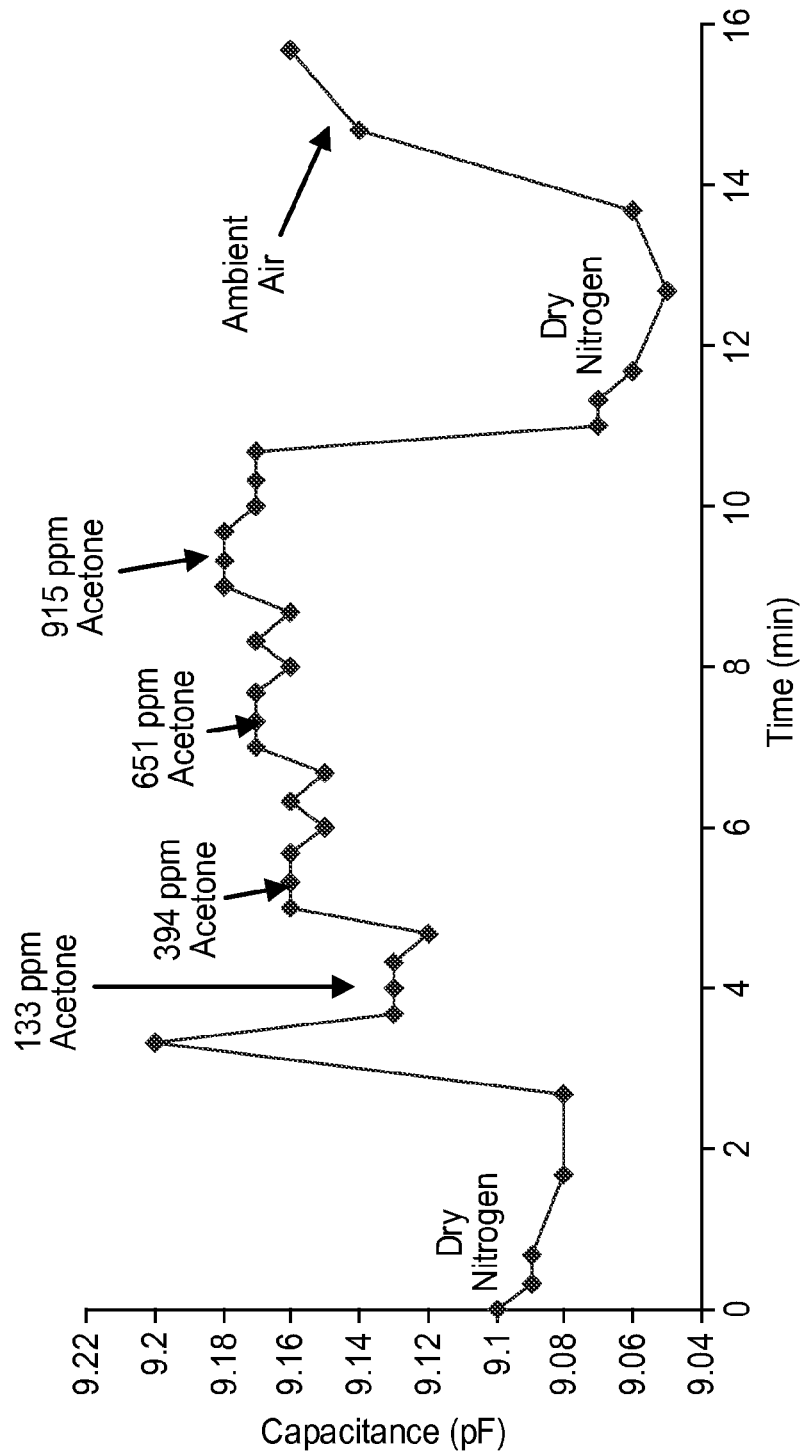
FIG. 6 is a plot of the measured capacitance of an exemplary sensing element of an interdigitated configuration, as a function of time of exposure to various levels of an organic analyte.

Sample 3 (prepared as described above) was tested using the same set-up as described with reference to Sample 1. The changes in capacitance (in picoFarads) of the sample were monitored at a frequency of 20 kilohertz at specific time intervals during the test (as shown in FIG. 6). At the beginning of the vapor test the sample was placed in the unsealed test chamber in order to measure the initial capacitance of the sample at ambient room conditions (air, 40% relative humidity, not shown in FIG. 6). The sample was then exposed to dry nitrogen (8% relative humidity, 20° C.). The test chamber was sealed and a dry nitrogen stream containing 133 ppm of acetone was introduced into the test chamber (in FIG. 6, the peak in between the dry nitrogen exposure and the 133 ppm acetone exposure is an artifact). After a period of time at 133 ppm acetone, the concentration of acetone was increased to 394 ppm. After a period of time at 394 ppm, the concentration of acetone was increased to 651 ppm. After a period of time at 651 ppm, the concentration of acetone was increased to 915 ppm. After this, the sample was exposed to dry nitrogen. The test chamber was then opened, and the sample was exposed to ambient conditions (air, 40% relative humidity).

Testing of Sample 4

Figure 7:
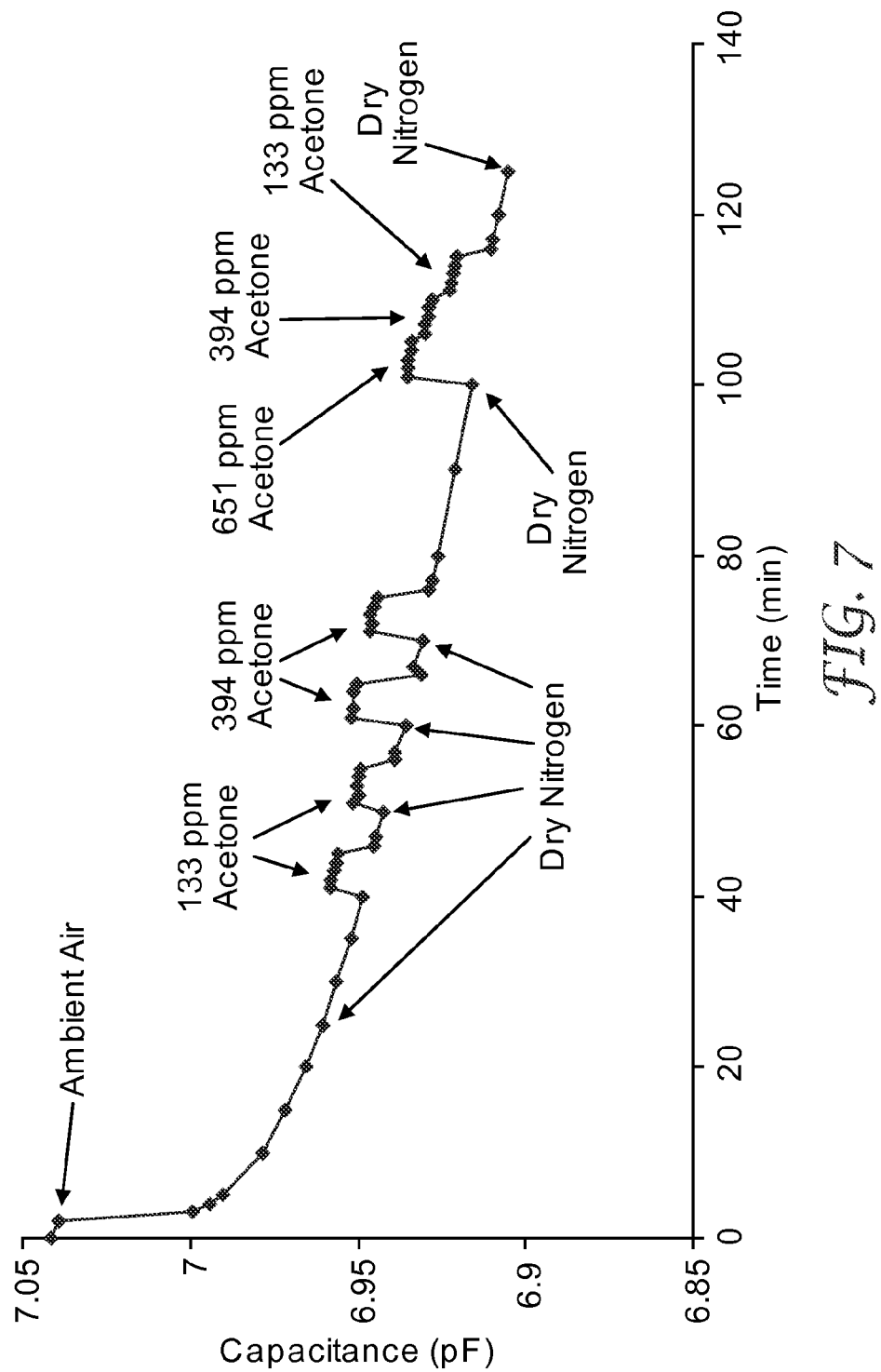
FIG. 7 is a plot of the measured capacitance of an exemplary sensing element of an interdigitated configuration, as a function of time of exposure to various levels of an organic analyte.

Sample 4 (prepared as described above) was tested using the same set-up as described with reference to Sample 1. The changes in capacitance (in picoFarads) of the sample were monitored at a frequency of 10 kilohertz at specific time intervals during the test (as shown in FIG. 7). At the beginning of the test, the sample was placed in the unsealed test chamber in order to measure the initial capacitance of the sample at ambient room conditions (air, approximately 50% relative humidity). The test chamber was sealed and, the sample was then exposed to dry nitrogen (approximately 8% relative humidity, 20° C.). A dry nitrogen stream containing 133 ppm of acetone was then introduced into the test chamber. Then, the test chamber was returned to a dry nitrogen environment. The exposure to 133 ppm of acetone was repeated followed by exposure to dry nitrogen. A dry nitrogen stream containing 394 ppm of acetone was then introduced into the test chamber. The test chamber was then returned to a dry nitrogen environment. The exposure to 394 ppm of acetone was repeated followed by exposure to dry nitrogen. After the dry nitrogen exposure, the sample was then exposed to a dry nitrogen stream with 651 ppm of acetone. After a period of time, the acetone concentration was reduced step-wise to 394 ppm and then to 133 ppm. Thereafter, the sample was exposed to dry nitrogen.

Testing of Sample 5

Figure 8:
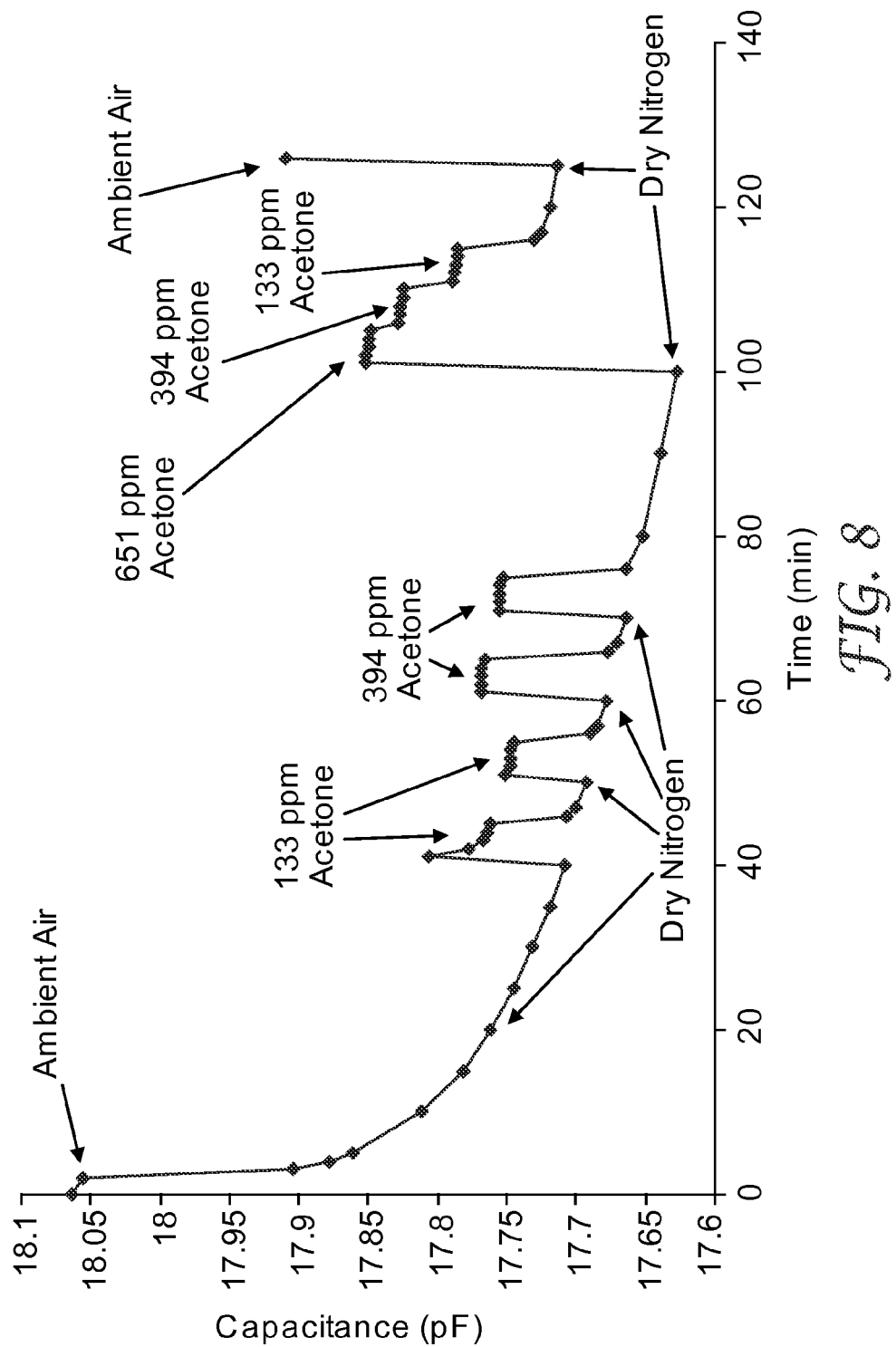
FIG. 8 is a plot of the measured capacitance of an exemplary sensing element of an interdigitated configuration, as a function of time of exposure to various levels of an organic analyte.

Sample 5 (prepared as described above) was tested using the same set-up as described with reference to Sample 1. The changes in capacitance (in picoFarads) of the sample were monitored at a frequency of 10 kilohertz at specific time intervals during the test (as shown in FIG. 8). At the beginning of the test, the sample was placed in the unsealed test chamber in order to measure the initial capacitance of the sample at ambient room conditions (air, approximately 52% relative humidity). The chamber was sealed and, the sample was then exposed to dry nitrogen (approximately 8% relative humidity, 20° C.). A dry nitrogen stream containing 133 ppm of acetone was then introduced into the test chamber. Then, the test chamber was returned to a dry nitrogen environment. The exposure to 133 ppm of acetone was repeated followed by exposure to dry nitrogen. A dry nitrogen stream containing 394 ppm of acetone was then introduced into the test chamber. The test chamber was then returned to a dry nitrogen environment. The exposure to 394 ppm of acetone was repeated followed by exposure to dry nitrogen. After the dry nitrogen exposure, the sample was then exposed to a dry nitrogen stream with 651 ppm of acetone. After a period of time, the acetone concentration was reduced step-wise to 394 ppm and then to 133 ppm. Thereafter, the sample was exposed to dry nitrogen. The test chamber was then opened, and sample was exposed to ambient conditions (air, 50% relative humidity).

Testing of Sample 6

Figure 9:
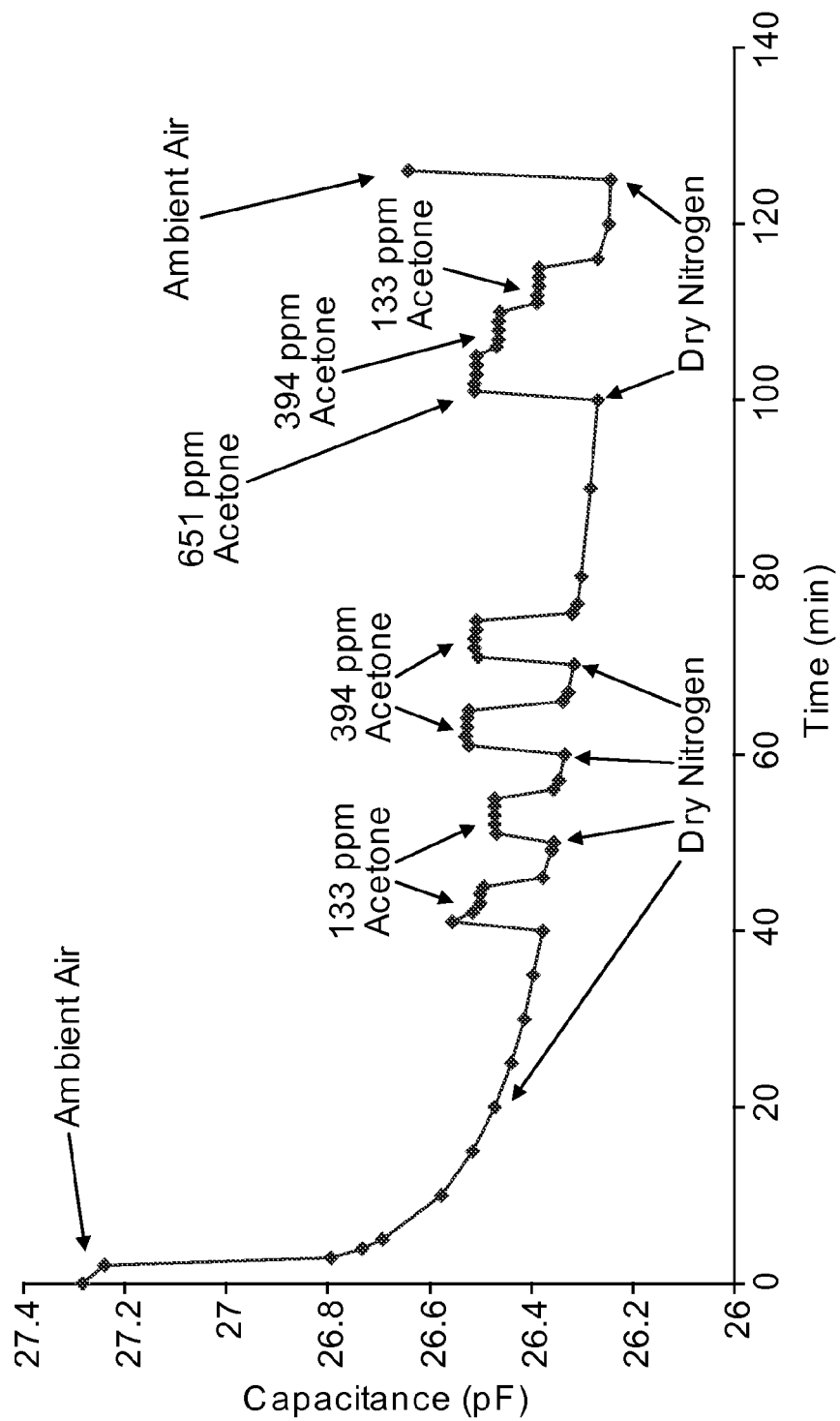
FIG. 9 is a plot of the measured capacitance of an exemplary sensing element of an interdigitated configuration, as a function of time of exposure to various levels of an organic analyte.

Sample 6 (prepared as described above) was tested using the same set-up as described with reference to Sample 1. The changes in capacitance (in picoFarads) of the sample were monitored at a frequency of 10 kilohertz at specific time intervals during the test (as shown in FIG. 9). At the beginning of the test, the sample was placed in the unsealed test chamber in order to measure the initial capacitance of the sample at ambient room conditions (air, approximately 71% relative humidity). The test chamber was sealed and, the sample was then exposed to dry nitrogen (approximately 8% relative humidity, 20° C.). A dry nitrogen stream containing 133 ppm of acetone was then introduced into the test chamber. Then, the test chamber was returned to a dry nitrogen environment. The exposure to 133 ppm of acetone was repeated followed by exposure to dry nitrogen. A dry nitrogen stream containing 394 ppm of acetone was then introduced into the test chamber. The test chamber was then returned to a dry nitrogen environment. The exposure to 394 ppm of acetone was repeated followed by exposure to dry nitrogen. After the dry nitrogen exposure, the sample was then exposed to a dry nitrogen stream with 651 ppm of acetone. After a period of time, the acetone concentration was reduced step-wise to 394 ppm and then to 133 ppm. Thereafter, the sample was exposed to dry nitrogen. The test chamber was then opened, and the sample was exposed to ambient conditions (air, 71% relative humidity).

Testing of Sample 7

Figure 10:
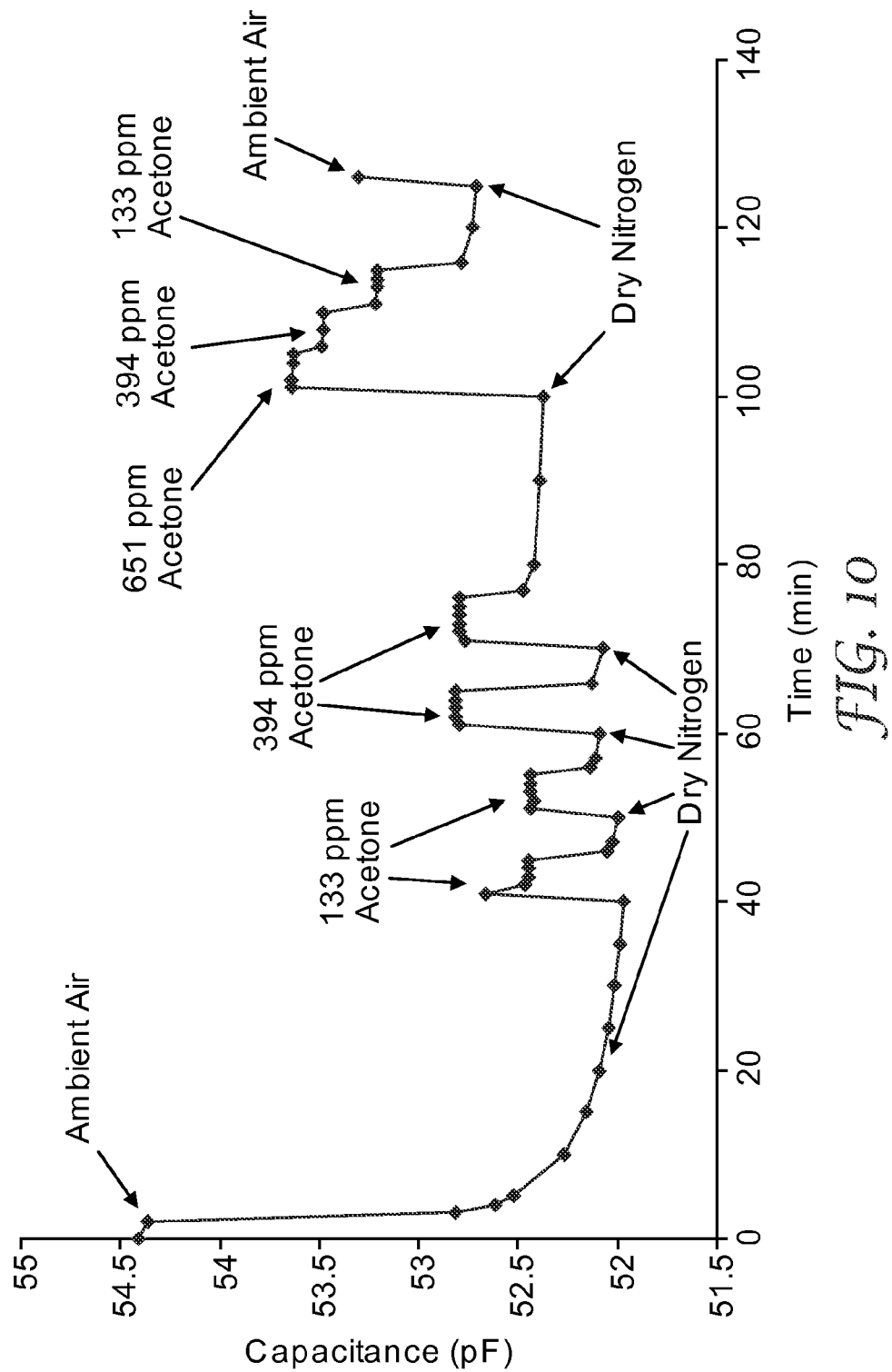
FIG. 10 is a plot of the measured capacitance of an exemplary sensing element of an interdigitated configuration, as a function of time of exposure to various levels of an organic analyte.

Sample 7 (prepared as described above) was tested using the same set-up as described with reference to Sample 1. The changes in capacitance (in picoFarads) of the sample were monitored at a frequency of 10 kilohertz at specific time intervals during the test (as shown in FIG. 10). At the beginning of the test, the sample was placed in the unsealed test chamber in order to measure the initial capacitance of the sample at ambient room conditions (air, approximately 74% relative humidity). The test chamber was sealed and, the sample was then exposed to dry nitrogen (approximately 8% relative humidity, 20° C.). A dry nitrogen stream containing 133 ppm of acetone was then introduced into the test chamber. Then, the test chamber was returned to a dry nitrogen environment. The exposure to 133 ppm of acetone was repeated followed by exposure to dry nitrogen. A dry nitrogen stream containing 394 ppm of acetone was then introduced into the test chamber. The test chamber was then returned to a dry nitrogen environment. The exposure to 394 ppm of acetone was repeated followed by exposure to dry nitrogen. After the dry nitrogen exposure, the sample was then exposed to a dry nitrogen stream with 651 ppm of acetone. After a period of time, the acetone concentration was reduced step-wise to 394 ppm and then to 133 ppm. Thereafter, the sample was exposed to dry nitrogen. The test chamber was then opened, and the sample was exposed to ambient conditions (air, 71% relative humidity).

Testing of Sample 8

Figure 11:
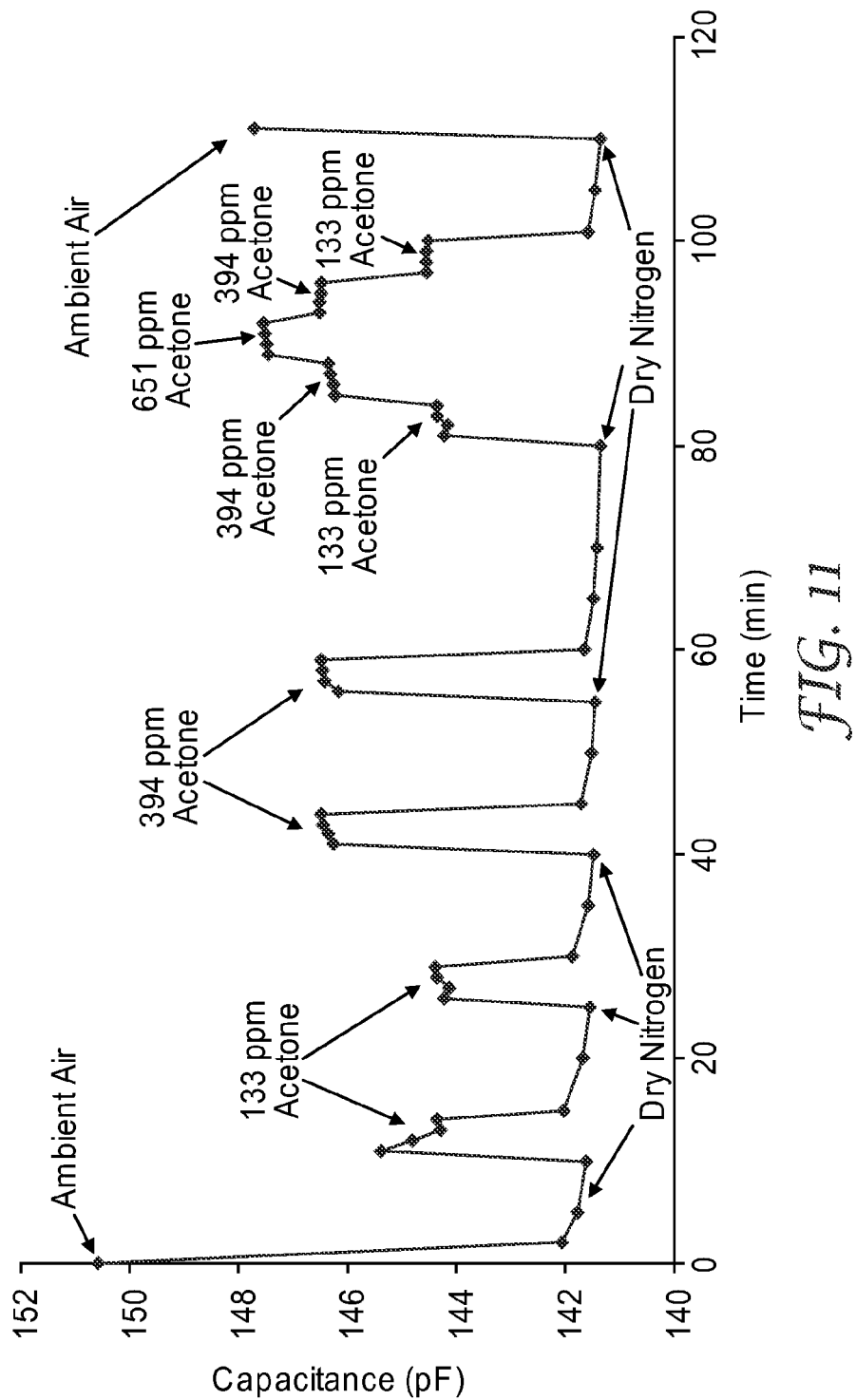
FIG. 11 is a plot of the measured capacitance of an exemplary sensing element of an interdigitated configuration, as a function of time of exposure to various levels of an organic analyte.

Sample 8 (prepared as described above) was tested using the same set-up as described with reference to Sample 1. The changes in capacitance (in picoFarads) of the sample were monitored at a frequency of 200 kilohertz at specific time intervals during the test (as shown in FIG. 11). At the beginning of the test, the sample was placed in the unsealed test chamber in order to measure the initial capacitance of the sample at ambient room conditions (air, approximately 66% relative humidity). The test chamber was sealed and, the sample was then exposed to dry nitrogen (approximately 8% relative humidity, 20° C.). A dry nitrogen stream containing 133 ppm of acetone was then introduced into the test chamber. Then, the test chamber was returned to a dry nitrogen environment. The exposure to 133 ppm of acetone was repeated followed by exposure to dry nitrogen. A dry nitrogen stream containing 394 ppm of acetone was then introduced into the test chamber. The test chamber was then returned to a dry nitrogen environment. The exposure to 394 ppm of acetone was repeated followed by exposure to dry nitrogen. After the dry nitrogen exposure, the sample was then exposed to a dry nitrogen stream with 133 ppm of acetone. After a period of time, the acetone concentration was increased step-wise to 394 ppm and then to 651 ppm. After a period of time at 651 ppm of acetone, the acetone concentration was reduced step-wise to 394 ppm and then to 133 ppm. Thereafter, the sample was exposed to dry nitrogen. The test chamber was then opened, and the sample was exposed to ambient conditions (air, 65% relative humidity).

Testing of Sample 9

Figure 12:
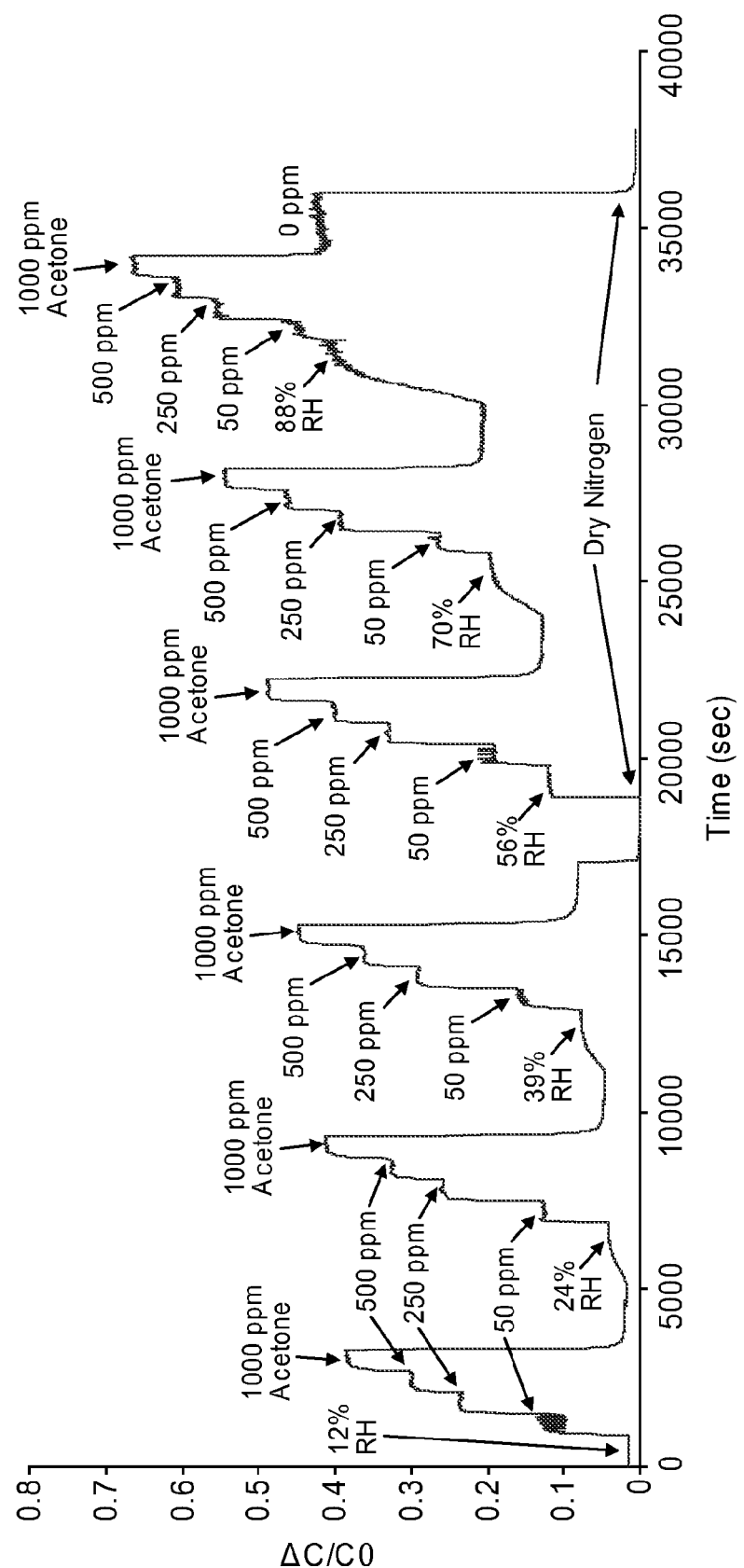
FIG. 12 is a plot of the measured capacitance of an exemplary sensing element of a parallel-plate configuration, as a function of time of exposure to various levels of an organic analyte.

Sample 9 (prepared as described above) was tested using the same set-up as described with reference to Sample 1. The changes in capacitance (in nanoFarads) of the sample were monitored at a frequency of 1 kilohertz at specific time intervals during the test. The data is plotted in FIG. 12 as a change of capacitance ratio ($\Delta C/C_o$) over time (as opposed to the absolute capacitance). The sample was placed in the test chamber, and the test chamber was sealed. The sample was then exposed to dry nitrogen (approximately 8% relative humidity, 20° C.; not shown in FIG. 12). The capacitance of the sample under these dry nitrogen conditions was used as the $C_o$ value throughout the experiment. The entire experiment was performed at a fixed temperature of 20° C. and thus the relative humidity values were calculated at that temperature. The sample was then exposed to a nitrogen stream containing 12% relative humidity. After a period of time, the sample was exposed to a nitrogen stream containing 12% relative humidity and 50 ppm of acetone. Keeping the relative humidity fixed at 12%, the acetone concentration was increased sequentially to 250, 500 and 1000 ppm. The test chamber was then returned to the 12% relative humidity nitrogen environment. After a period of time, the relative humidity in the nitrogen stream was increased to 24%. The sample was then exposed sequentially to increasing concentrations of acetone (50, 250, 500 and 1000 ppm) at a fixed relative humidity of 24%. The test chamber was then returned to the 24% relative humidity nitrogen environment. After a period of time, the relative humidity in the nitrogen stream was increased to 39%. The sample was then exposed sequentially to increasing concentrations of acetone (50, 250, 500 and 1000 ppm) at a fixed relative humidity of 39%. The test chamber was then returned to the 39% relative humidity nitrogen environment. The test chamber was then returned to a dry nitrogen environment (8% relative humidity). After a period of time, the relative humidity in the nitrogen stream was increased to 56%. The sample was then exposed sequentially to increasing concentrations of acetone (50, 250, 500 and 1000 ppm) at a fixed relative humidity of 56%. The test chamber was then returned to the 56% relative humidity nitrogen environment. After a period of time, the relative humidity in the nitrogen stream was increased to 70%. The sample was then exposed sequentially to increasing concentrations of acetone (50, 250, 500 and 1000 ppm) at a fixed relative humidity of 70%. The test chamber was then returned to the 70% relative humidity nitrogen environment. After a period of time, the relative humidity in the nitrogen stream was increased to 88%. The sample was then exposed sequentially to increasing concentrations of acetone (50, 250, 500 and 1000 ppm) at a fixed relative humidity of 88%. The sample was then exposed to a gaseous stream containing 0 ppm acetone, at 88% relative humidity. The sample was then returned to a dry nitrogen environment (8% relative humidity).

Testing of Sample 10

Figure 13:
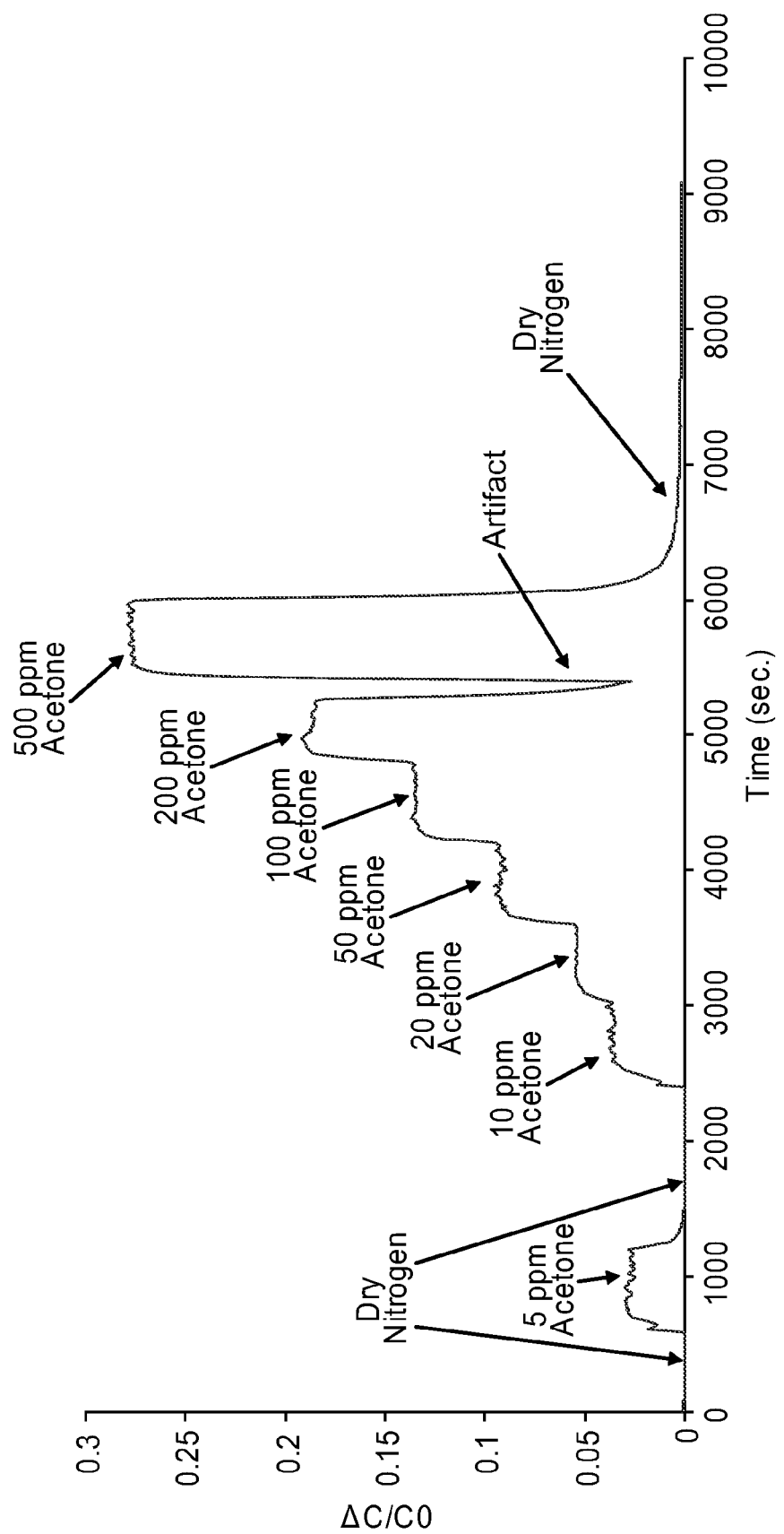
FIG. 13 is a plot of the measured capacitance of an exemplary sensing element of a parallel-plate configuration, as a function of time of exposure to various levels of an organic analyte.

Sample 10 (prepared as described above) was tested using the same set-up as described with reference to Sample 1. The changes in capacitance (in nanoFarads) of the sample were monitored at a frequency of 1 kilohertz at specific time intervals during the test. The data is plotted in FIG. 13 as a change of capacitance ratio ($\Delta C/C_o$) over time. The sample was placed in the test chamber, and the test chamber was sealed. The sample was then exposed to dry nitrogen (approximately 8% relative humidity, 20° C.). The capacitance of the sample under these dry nitrogen conditions was used as the $C_o$ value throughout the experiment. A dry nitrogen stream containing 5 ppm of acetone was introduced into the test chamber. Then, the test chamber was returned to a dry nitrogen environment. The sample was then exposed to a dry nitrogen stream containing 10 ppm of acetone. After a period of time, the acetone concentration was increased to 20 ppm. Thereafter, the sample was exposed to successive nitrogen streams containing 50, 100, 200 and 500 ppm of acetone. The sample was then returned to a dry nitrogen environment. (In FIG. 13, the drop in capacitance ratio between the 200 and 500 ppm acetone exposures is an artifact caused by an issue in the delivery of the analyte.)

Testing of Sample 11

Figure 14:
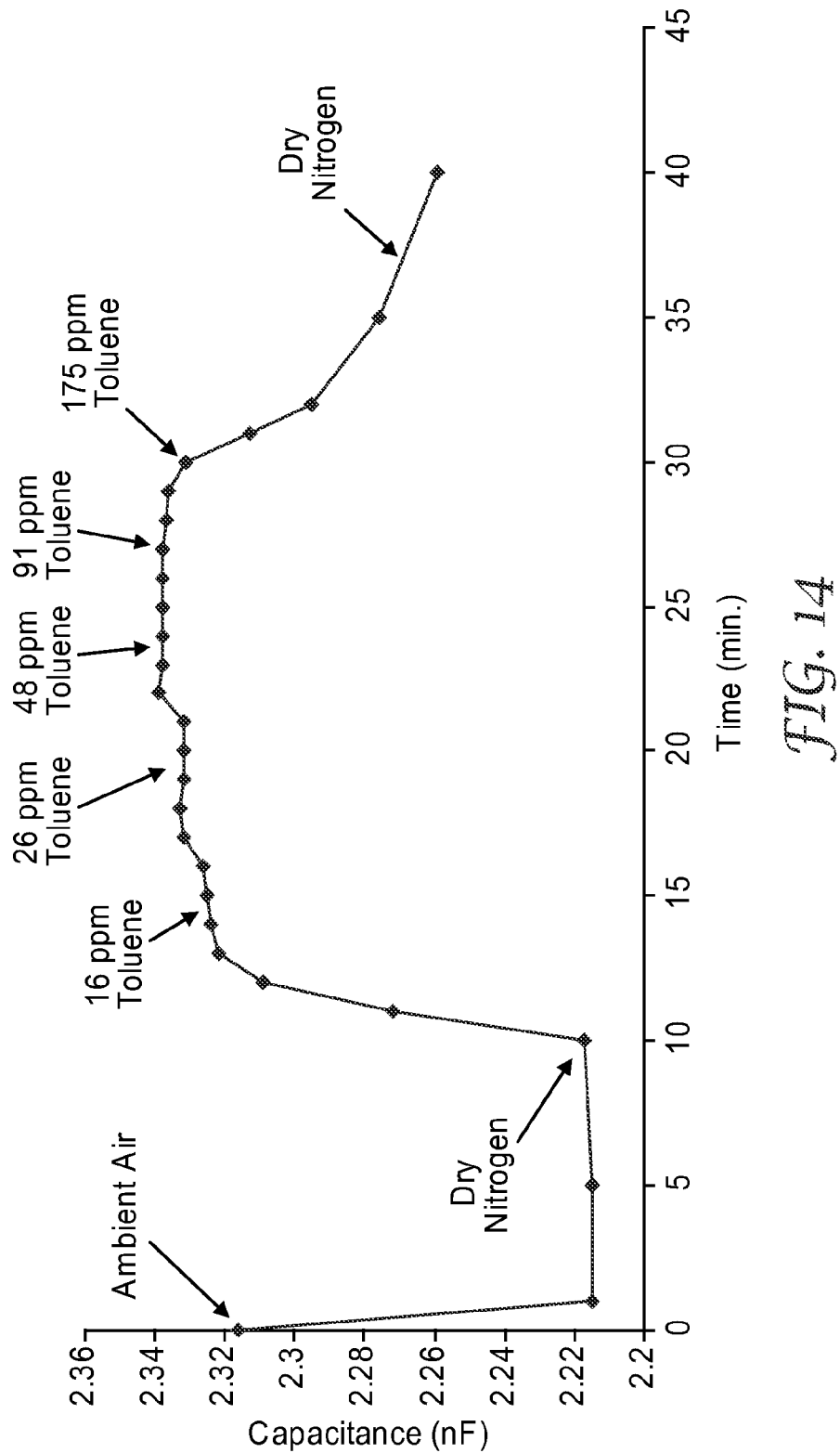
FIG. 14 is a plot of the measured capacitance of an exemplary sensing element of a parallel-plate configuration, as a function of time of exposure to various levels of an organic analyte.

A new sample, prepared in similar manner to that described in Preparation of Sample 2, was tested for response to toluene using the same set-up described with reference to Sample 1. The changes in capacitance (in nanoFarads) of the sample were monitored at a frequency of 1 kilohertz at specific time intervals during the test (as shown in FIG. 14). At the beginning of the test, the sample was placed in the unsealed test chamber in order to measure the initial capacitance of the sample at ambient room conditions (air, approximately 29% relative humidity). The test chamber was sealed, and the sample was exposed to dry nitrogen (approximately 8% relative humidity, 20° C.). A dry nitrogen stream containing 16 ppm of toluene was then introduced into the test chamber. After a period of time, the toluene concentration was increased to 26 ppm. Thereafter, the sample was exposed to successive nitrogen streams containing 48, 91 and 175 ppm of toluene. The sample was then returned to a dry nitrogen environment.

Testing of Sample 12

Figure 15:
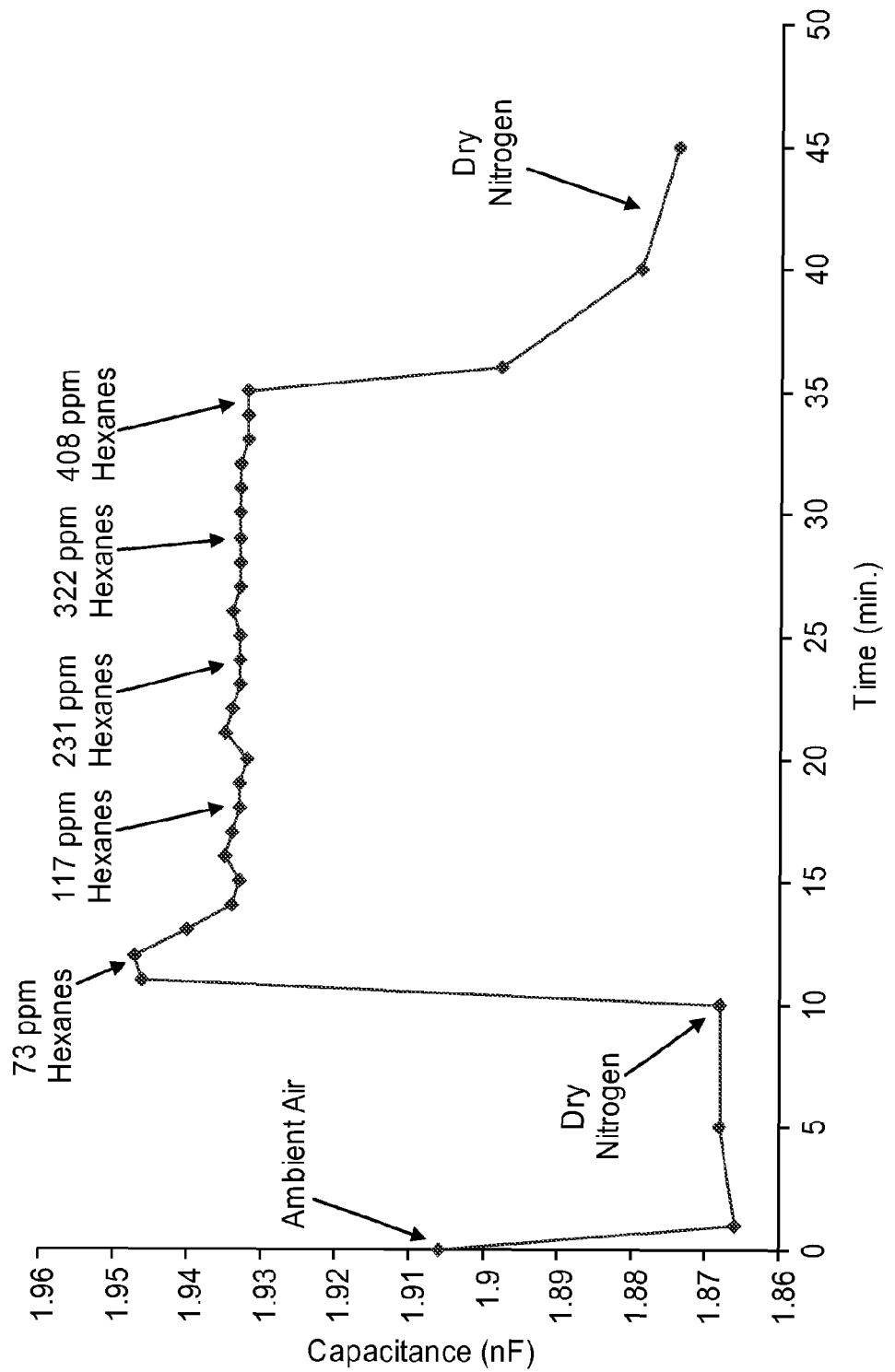
FIG. 15 is a plot of the measured capacitance of an exemplary sensing element of a parallel-plate configuration, as a function of time of exposure to various levels of an organic analyte.

A new sample, prepared in similar manner to that described in Preparation of Sample 2, was tested for response to hexanes using the same set-up described with reference to Sample 1. The changes in capacitance (in nanoFarads) of the sample were monitored at a frequency of 1 kilohertz at specific time intervals during the test (as shown in FIG. 15). At the beginning of the test the sample was placed in the unsealed test chamber in order to measure the initial capacitance of the sample at ambient room conditions (air, approximately 23% relative humidity). The chamber was sealed, and the sample was then exposed to dry nitrogen (approximately 8% relative humidity, 20° C.). A dry nitrogen stream containing 73 ppm of hexanes was then introduced into the test chamber. After a period of time, the hexanes concentration was increased to 117 ppm. Thereafter, the sample was exposed to successive nitrogen streams containing 231, 322 and 408 ppm of hexanes. The sample was then returned to a dry nitrogen environment.

Testing of Sample 13

Figure 16:
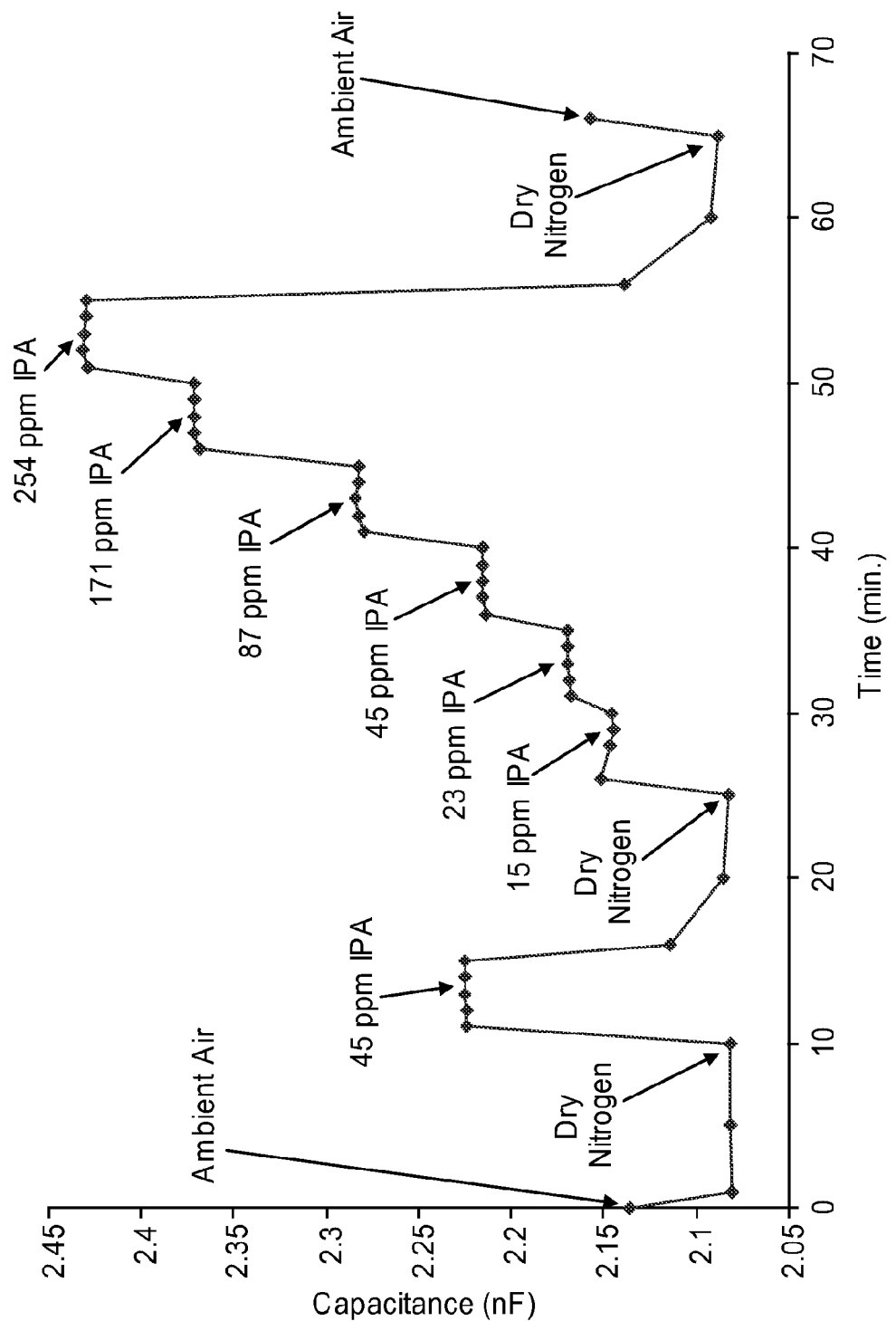
FIG. 16 is a plot of the measured capacitance of an exemplary sensing element of a parallel-plate configuration, as a function of time of exposure to various levels of an organic analyte.

A new sample, prepared in similar manner to that described in Preparation of Sample 2, was tested for response to isopropyl alcohol (IPA) using the same set-up described with reference to Sample 1. The changes in capacitance (in nanoFarads) of the sample were monitored at a frequency of 1 kilohertz at specific time intervals during the test (as shown in FIG. 16). At the beginning of the test the sample was placed in the unsealed test chamber in order to measure the initial capacitance of the sample at ambient room conditions (air, approximately 23% relative humidity). The test chamber was sealed, and the sample was then exposed to dry nitrogen (approximately 8% relative humidity, 20° C.). A dry nitrogen stream containing 45 ppm of isopropyl alcohol (IPA) was introduced into the test chamber. Then, the test chamber was returned to a dry nitrogen environment. The sample was then exposed to a dry nitrogen stream containing 15 ppm of IPA. After a period of time, the IPA concentration was increased to 23 ppm. Thereafter, the sample was exposed to successive nitrogen streams containing 45, 87, 171 and 254 ppm of IPA. The sample was then returned to a dry nitrogen environment. The test chamber was then opened, and the sample was exposed to ambient conditions (air, 26% relative humidity).

A number of embodiments of the invention have been described. Nevertheless, it will be understood that various modifications may be made without departing from the invention. Accordingly, other embodiments are within the scope of the following claims.

What is claimed is:

1. A sensing element for sensing an organic chemical analyte, comprising:
   a first electrode and a second electrode; and,
   a microporous, hydrophobic, analyte-responsive dielectric material disposed at least in proximity to the first and second electrodes, wherein the microporous, hydrophobic analyte-responsive dielectric material is a polymer of intrinsic microporosity comprised of organic macromolecules comprised of generally planar species connected by rigid linkers, said rigid linkers having a point of contortion such that two adjacent planar species connected by the linker are held in non-coplanar orientation.

2. The sensing element of claim 1 wherein the polymer of intrinsic microporosity comprises organic macromolecules comprised of first generally planar species connected by rigid linkers predominantly to a maximum of two other said first species, said rigid linkers having a point of contortion such that two adjacent first planar species connected by the linker are held in non-coplanar orientation.

3. The sensing element of claim 1 wherein the point of contortion is a spiro group, a bridged ring moiety or a sterically congested single covalent bond around which there is restricted rotation.

4. The sensing element of claim 1 in which at least one of the electrodes is permeable to an organic chemical analyte.

5. The sensing element of claim 4 wherein the permeable electrode comprises a discontinuous layer of conductive material.

6. The sensing element of claim 5 wherein the permeable electrode comprises a patterned layer of conductive material.

7. The sensing element of claim 1 wherein the sensing element comprises a parallel-plate capacitor configuration.

8. The sensing element of claim 1 wherein the sensing element comprises an interdigitated capacitor configuration.

9. The sensing element of claim 1 wherein the sensing element comprises a backing in proximity to at least one of the electrodes.

10. The sensing element of claim 1 wherein the sensing element comprises a cover layer in proximity to at least one of the electrodes.

11. The sensing element of claim 10 wherein the cover layer is permeable to an organic chemical analyte.

12. A sensor for sensing an organic chemical analyte, comprising:
   a sensing element that comprises a first electrode and a second electrode and a microporous, hydrophobic, analyte-responsive dielectric material disposed at least in proximity to the first and second electrodes, wherein the microporous, hydrophobic analyte-responsive dielectric material is a polymer of intrinsic microporosity comprised of organic macromolecules comprised of generally planar species connected by rigid linkers, said rigid linkers having a point of contortion such that two adjacent planar species connected by the linker are held in non-coplanar orientation; and, an operating circuit in electrical communication with the first and second electrodes, wherein the operating circuit is capable of applying a voltage to the first and second electrodes and is capable of detecting a change in an electrical property of the sensing element.

13. The sensor of claim 12 wherein the polymer of intrinsic microporosity comprises organic macromolecules comprised of first generally planar species connected by rigid linkers predominantly to a maximum of two other said first species, said rigid linkers having a point of contortion such that two adjacent first planar species connected by the linker are held in non-coplanar orientation.

14. The sensor of claim 12 wherein the point of contortion is a spiro group, a bridged ring moiety or a sterically congested single covalent bond around which there is restricted rotation.

15. The sensor of claim 12 in which at least one of the electrodes is permeable to an organic chemical analyte.

16. A method of sensing organic chemical analytes, comprising:
providing a sensor that comprises;
a sensing element that comprises a first electrode and a second electrode and a microporous, hydrophobic, analyte-responsive dielectric material disposed at least in proximity to the first and second electrodes, wherein the microporous, hydrophobic analyte-responsive dielectric material is a polymer of intrinsic microporosity comprised of organic macromolecules comprised of generally planar species connected by rigid linkers, said rigid linkers having a point of contortion such that two adjacent planar species connected by the linker are held in non-coplanar orientation; and,
an operating circuit in electrical communication with the first and second electrodes, wherein the operating circuit is capable of applying a voltage to the first and second electrodes and is capable of detecting a change in an electrical property of the sensing element;
exposing the sensing element to an environment potentially containing one or more organic chemical analytes;
applying a voltage to the first and second electrodes; and,
monitoring an electrical property of the sensing element.

17. The method of claim 16 wherein the sensing element comprises a capacitor, and wherein the electrical property that is monitored is an capacitive property of the sensing element.

18. The method of claim 17 wherein the property that is measured is the capacitance of the sensing element.

* * * * *

UNITED STATES PATENT AND TRADEMARK OFFICE
CERTIFICATE OF CORRECTION

PATENT NO. : 8,835,180 B2  
APPLICATION NO. : 12/681741  
DATED : September 16, 2014  
INVENTOR(S) : Stefan Gryska Page 1 of 1

It is certified that error appears in the above-identified patent and that said Letters Patent is hereby corrected as shown below:

Title Page, Column 2, item (56), (Other Publications)
Line 1, Delete "Polyp" and insert -- Poly --, therefor.

Title Page, Column 2, item (56), (Other Publications)
Line 2, Delete "proprties" and insert -- properties --, therefor.

In the Specification

Column 8
Line 64, Delete "microscopically" and insert -- macroscopically --, therefor.

Signed and Sealed this
Twenty-fourth Day of February, 2015

Michelle K. Lee
*Deputy Director of the United States Patent and Trademark Office*